United States Patent [19]

Pascal et al.

[11] Patent Number: 5,082,847
[45] Date of Patent: Jan. 21, 1992

[54] CARBOSTYRIL COMPOUNDS CONNECTED VIA AN OXYALKYL GROUP WITH A PIPERIDINE RING AND HAVING PHARMACEUTICAL UTILITY

[75] Inventors: Jean-Claude Pascal, Cachan, France; Leslie Patmore, Edinburgh, Scotland; Jurg Pfister, Los Altos, Calif.; Dominique Blondet, Paris; John M. Armstrong, Saint Remy les Chevreuse, both of France

[73] Assignee: Syntex (U.S.A.) Inc., Palo Alto, Calif.

[21] Appl. No.: 555,201

[22] Filed: Jul. 18, 1990

[51] Int. Cl.$^5$ .................. C07D 215/22; A61K 31/47
[52] U.S. Cl. .................... 514/312; 546/158
[58] Field of Search .................. 546/158; 514/312

[56] References Cited

U.S. PATENT DOCUMENTS

| 4,210,753 | 7/1980 | Tominaaga et al. | 544/128 |
| 4,427,680 | 2/1984 | Friebe et al. | 424/258 |
| 4,460,586 | 7/1984 | Berthold | 424/250 |
| 4,482,560 | 11/1984 | Banno et al. | 424/258 |

FOREIGN PATENT DOCUMENTS

| 50-106977 | of 1974 | Japan . |
| 50-142576 | of 1974 | Japan . |
| 52-108980 | of 1976 | Japan . |
| 55089221 | of 1978 | Japan . |
| 57-018674 | of 1982 | Japan . |
| 63-290821 | of 1987 | Japan . |

OTHER PUBLICATIONS

Derivatives of 3,4-Dihydrocarbostyril as β-Adrenergic Blocking Agents by Nakagawa et al., J. Med. Chem., 17, 529-533 (1974).

*Primary Examiner*—Jane T. Fan
*Assistant Examiner*—Zinna Northington-Davis
*Attorney, Agent, or Firm*—Brian Lewis; David A. Lowin; Tom M. Moran

[57] ABSTRACT

Carbostyril derivatives of Formula I:

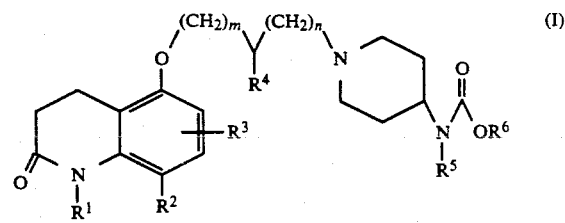

wherein:
m is 0, 1, or 2;
n is 0, 1, or 2;
$R^1$ is hydrogen or lower alkyl;
$R^2$ is hydrogen, halogen, hydroxy, lower alkyl, lower alkoxy, aralkoxy, or acyloxy;
$R^3$ is hydrogen, halogen, lower alkyl, or lower alkoxy;
$R^4$ is hydrogen, hydroxy, lower alkyl, acyloxy, provided that when $R^4$ is hydroxy or acyloxy, m and n are both 1;
$R^5$ is hydrogen or lower alkyl; and
$R^6$ is alkyl, hydroxyalkyl, alkoxyalkyl, or (dialkylamino)alkyl;

and the pharmaceutically acceptable acid addition salts and N-oxides (at the carbostyril nitrogen) thereof, and compositions containing them, are useful in treating cardiovascular diseases, particularly arrhythmias. Methods of preparing intermediates, the compounds, their formulations and methods of treatment therewith are also disclosed.

77 Claims, No Drawings

CARBOSTYRIL COMPOUNDS CONNECTED VIA AN OXYALKYL GROUP WITH A PIPERIDINE RING AND HAVING PHARMACEUTICAL UTILITY

BACKGROUND OF THE INVENTION

1. Field of the Invention

This invention is concerned with carbostyril derivatives useful in treating cardiovascular diseases, particularly in treating arrhythmias.

2. Background to the Invention

Carbostyril derivatives are disclosed in the patent literature as having cardiotonic, anti-arrhythmic, α- and β-adrenoceptor blocking activities, and as being calcium antagonist, antihistaminic and local anesthetic agents. See, for example, U.S. Pat. Nos. 4,210,753 and 4,482,560, and Japanese Kokai Tokyo Koho Sho 57-018,674 (Derwent Abstract 18695E/10).

SUMMARY OF THE INVENTION

A first aspect of this invention comprises carbostyril derivatives of Formula I:

wherein:
m is 0, 1, or 2;
n is 0, 1, or 2;
$R^1$ is hydrogen or lower alkyl;
$R^2$ is hydrogen, halogen, hydroxy, lower alkyl, lower alkoxy, aralkoxy, or acyloxy;
$R^3$ is hydrogen, halogen, lower alkyl, or lower alkoxy;
$R^4$ is hydrogen, hydroxy, lower alkyl, or acyloxy, provided that when $R^4$ is hydroxy or acyloxy, m and n are both 1;
$R^5$ is hydrogen or lower alkyl; and
$R^6$ is alkyl, hydroxyalkyl, alkoxyalkyl, or (dialkylamino)alkyl;
and the pharmaceutically acceptable acid addition salts and N-oxides thereof.

A second aspect of this invention comprises pharmaceutical compositions containing at least one compound of Formula I and a pharmaceutically acceptable excipient.

A third aspect of this invention comprises methods for treating cardiovascular disease in a mammal by administering an effective amount of a compound of Formula I, or a composition containing it, to the mammal. In a preferred embodiment, the cardiovascular disease treated is a cardiac arrhythmia.

Further aspects of this invention are methods for preparing compounds of Formula I, including the single stereoisomers or mixtures of stereoisomers of the compounds of Formula I having a chiral center, as follows:

(a) contacting a compound, that is a single stereoisomer or a mixture of stereoisomers, of the formula:

wherein
$R^1$, $R^2$ and $R^3$ are as defined above,
with a compound of the formula:

wherein
$R^5$ and $R^6$ are as defined above, in a solvent that will dissolve both reactants; or (b) contacting a compound, or a single stereoisomer or a mixture of stereoisomers, of the formula:

wherein
$R^1$, $R^2$, $R^3$, m and n are as defined above,
$R^4$ is hydrogen or lower alkyl and Y is halo, with a compound of the formula:

wherein
$R^5$ and $R^6$ are as defined above, in the presence of a hydrogen halide acceptor; or (c) acylating a compound of Formula I wherein either $R^2$ or $R^4$ is OH, or $R^2$ and $R^4$ are both OH; or (d) saponifying a compound of Formula I wherein either $R^2$ or $R^4$ is —O—CO—alkyl, or $R^2$ and $R^4$ are both —O—CO—alkyl; or (e) deprotecting a compound of Formula I wherein $R^2$ is aralkoxy; or (f) resolving a racemic mixture of stereoisomers of Formula I into pure enantiomers using an appropriate optically active acid; or (g) converting a compound of Formula I in free base form to an acid addition salt by treatment with the appropriate organic or inorganic acid; or (h) decomposing an acid addition salt of a compound of Formula I to the corresponding free base by treatment with a suitable base or by treatment with a suitably loaded ion exchange resin; or (i) interchanging an acid addition salt of a compound of Formula I with another acid addition salt.

Still another aspect of the invention entails a process for preparing a 5-hydroxy-3,4-dihydrocarbostyril compound of Formula 5a:

(5a)

wherein:
R¹ is hydrogen or lower alkyl; and
R³ is hydrogen, lower alkyl, or lower alkoxy;
by hydrogenating a compound of the formula:

(9)

wherein R is lower alkyl.

Another aspect of the invention entails a process for preparing a 5-hydroxy-3,4-dihydrocarbostyril compound of Formula 5b:

(5b)

wherein:
R¹ is hydrogen or lower alkyl; and
R² is hydrogen, lower alkyl, or lower alkoxy;
by hydrogenating a compound of the formula:

(11)

wherein W is alkyl, aryl or cycloalkyl.

A still further aspect of the invention entails a process for preparing a 5-hydroxy-8-substituted-3,4-dihydrocarbostyril compound of Formula 5c:

(5c)

by cyclizing a compound of the formula:

(13)

wherein:
R is acetyl or phenylmethyl;
by contacting it with a strong acid at room temperature, to give a cyclized compound of the formula (14)

and hydrogenating the cyclized compound.

Other and further aspects of the invention will become apparant to those of ordinary skill in the art from the detailed description, preparations and examples that follow.

DETAILED DESCRIPTION OF THE INVENTION

Definitions

The following definitions are set forth to illustrate and define the meaning and scope of various terms used to describe the invention herein, unless otherwise stated or the context requires otherwise.

The term "alkyl" means a straight, branched, or cyclic saturated hydrocarbon radical having from 1 to 12 carbon atoms. Examples include methyl, ethyl, propyl, 1-methylethyl (isopropyl), butyl, 1,1-dimethylethyl (t-butyl), 2-methylpropyl (or "isobutyl"), pentyl, hexyl and heptyl, cyclopropyl, cyclopropylmethyl, cyclobutyl, cyclopentyl, cyclopentylmethyl, cyclohexyl, decyl, adamantoyl, dodecyl and the like. If more than one alkyl radical is present in a given molecule, each may be independently selected from "alkyl" unless otherwise stated.

The term "alkoxy" means the group R—O— wherein R is "alkyl" as defined above. Examples include methoxy, ethoxy, propoxy, 1,1-dimethylethoxy (tert-butoxy), pentyloxy, hexyloxy and the like.

The term "aryl" or "Ar—" refers to a substituted or unsubstituted monovalent unsaturated radical, for example, phenyl, which, if substituted, can have one or more lower alkyl, lower alkoxy, or halo groups in any available position on the ring.

The term "aralkoxy" means the group Ar—R—O— wherein R is alkyl as defined above.

The term "acyloxy" means the group R—C(O)—O— wherein R is alkyl as defined above.

The term "lower" modifies "alkyl" and "alkoxy" and refers to those radicals having four carbon atoms or less.

The term "halo" or "halogen" refers to fluoro, chloro, bromo or iodo.

The term "hydroxyalkyl" means the group HO—R— wherein R is alkyl as defined above.

The term "alkoxyalkyl" means the group R—O—R— wherein each R is independently alkyl as defined above.

The term "(dialkylamino)alkyl" means the group $R_2N$—R— wherein each R is independently alkyl as defined above.

The term "N-oxide" refers to the stable radical

at the carbostyril nitrogen.

The term "optional" or "optionally" means that the subsequently described event or circumstance may or may not occur, and that the description includes instances where the event or circumstance occurs and instances in which it does not. For example, "optionally substituted phenyl" means that the phenyl may or may not be substituted and that the description includes both unsubstituted phenyl and substituted phenyl; "optionally followed by converting the free base to the acid addition salt" means that the conversion may or may not be carried out in order for the process described to fall within the invention, and the invention includes those processes in which the free base is converted to the acid addition salt and those processes in which it is not.

The terms "inert organic solvent" or "inert solvent" means a solvent inert under the conditions of the reaction being described in conjunction therewith [including, for example, benzene, toluene, acetonitrile, tetrahydrofuran ("THF"), dimethylformamide ("DMF"), chloroform, methylene chloride (or dichloromethane), diethyl ether, pyridine and the like]. Unless specified to the contrary, the solvents used in the reactions of the present invention are inert organic solvents.

The term "arrhythmia" means any variation from the normal rhythm of the heartbeat, including supraventricular premature beat, heart block (first and second degree and complete), atrial fibrillation, atrial flutter, atrial tachyarrhythmia of other etiology, atrioventricular nodal or atrioventricular junctional arrhythmias, ventricular premature beats (unifocal and multifocal), torsades de pointes, ventricular tachyarrhythmia, and ventricular fibrillation.

The term "mammal" includes both humans and nonhuman mammals (e.g. domestic and farm animals, such as cats, dogs, sheep, cattle, horses, and the like), especially, humans.

The term "treatment" or "treating" means any treatment of a disease in a mammal, and includes:

(i) preventing the disease, i.e., causing the clinical symptoms of the disease not to develop;

(ii) inhibiting the disease, i.e., arresting the development of clinical symptoms; and/or (iii) relieving the disease, i.e., causing the regression of clinical symptoms.

The term "therapeutically effective amount" is that amount which, when administered, is sufficient to effect treatment, as defined above.

"Pharmaceutically acceptable acid addition salts" means those salts that retain the biological effectiveness and properties of the parent compounds and are not biologically or otherwise undesirable. Pharmaceutically acceptable acid addition salts may be formed with inorganic acids, such as hydrochloric acid, hydrobromic acid, sulfuric acid, nitric acid, phosphoric acid, and the like, and with organic acids such as acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, para-toluenesulfonic acid, salicylic acid, and the like. The salts may be single or multiple salts of one or more anions, e.g., from the above-described acids.

Compounds that have identical molecular formulae but differ in the nature or sequence of bonding of their atoms or in the arrangement of their atoms in space are termed "isomers". Isomers are termed "stereoisomers" when they differ only in the arrangement of their atoms in space, and "constitutional isomers" when they differ in the nature and sequence of bonding of their atoms. Because constitutional isomers are considered in normal chemical usage to be different compounds (such as, for example, dimethyl ether and ethanol, which are constitutional isomers of molecular formula $C_2H_6O$), the term "isomer" is frequently used instead of "stereoisomer". Stereoisomers may be "achiral" (when a molecule is superimposable on its mirror image) or "chiral" (when it is not); and chiral stereoisomers are sometimes referred to as "optical isomers". Stereoisomers that are mirror images of one another are termed "enantiomers"; stereoisomers that are not mirror images are termed "diastereomers". A compound of Formula I in which $R^4$ is not hydrogen is chiral, having the carbon atom to which $R^4$ is attached as its center of chirality (that atom being sometimes referred to as an "asymmetric" carbon atom). When a compound has only one chiral center, a pair of enantiomers of opposite chirality is possible; and these enantiomers may be characterized and described in various ways, such as by the absolute configuration of the chiral center (using the R- and S- sequencing rules of Cahn and Prelog, and describing the compounds as (R)- and (S)-isomers), or by the rotation of polarized light by the molecule (and describing the compounds as (+)- and (−)-isomers). Such a compound may exist as individual enantiomers or as a mixture, especially a racemic mixture (i.e. a mixture containing equal proportions of the enantiomers, described as an (RS)- or (±)-mixture), thereof. Conventions for stereochemical nomenclature, and methods for the determination of stereochemistry and the separation of stereoisomers, are well-known in the art (as exemplified by the discussion in, for example, Chapter 4 of "Advanced Organic Chemistry", 3rd edition, March, Jerry, John Wiley and Sons, New York, 1985). Unless indicated otherwise, the description or naming of a particular compound of Formula I in the specification and claims is intended to include both enantiomers and mixtures, racemic or otherwise, thereof.

The compounds of Formula I are named and numbered as illustrated below. For example, the compound where m=n=1, $R^1$, $R^2$, $R^3$ and $R^5$ are H, $R^4$ is OH, and $R^6$ is 2-methylpropyl (or isobutyl), i.e., the compound of Formula II, is named 3,4-dihydro-5-[2-hydroxy-3-(4-((2-methylpropoxy)carbonylamino)-1-piperidyl)propoxy]carbostyril.

The compound where m=n=1, $R^1$, $R^3$ and $R^5$ are H, $R^2$ is Cl, $R^4$ is OH, and $R^6$ is cyclopropylmethyl is named 8-chloro-3,4-dihydro-5-[2-hydroxy-3-(4-((cyclopropylmethoxy)carbonylamino)-1-piperidyl)propoxy]carbostyril.

The compound where m=n=1, $R^1$, $R^3$ and $R^4$ are H, $R^2$ is methoxy, $R^5$ is methyl, and $R^6$ is 2-methoxyethyl is named 3,4-dihydro-8-methoxy-5-[3-(4-((2-methoxyethoxy) carbonyl-N-methylamino)-1-piperidyl)propoxy]carbostyril.

The N-oxide of the compound where m=n=1, $R^1$, $R^2$, $R^3$ and $R^5$ are H, $R^4$ is OH, and $R^6$ is 2-(dimethylamino)ethyl is named 3,4-dihydro-5-[2-hydroxy-3-(4-((2-dimethylaminoethoxy)carbonylamino)-1-piperidyl)propoxy]carbostyril N-oxide.

The compound where m=1, n=0, $R^1$, $R^3$, $R^4$ and $R^5$ are H, $R^2$ is methoxy, and $R^6$ is cyclopropylmethyl is named 3,4-dihydro-8-methoxy-5-[2-(4-((cyclopropylmethoxy)carbonylamino)-1-piperidyl)ethoxy]carbostyril.

The compound where m=n=2, $R^1$ and $R^4$ are H, $R^2$ and $R^3$ (at the 6-position) are methoxy, $R^5$ is methyl, and $R^6$ is 2-methoxyethyl is named 3,4-dihydro-6,8-dimethoxy-5-[5-(4-((2-methoxyethoxy)carbonyl-N-methylamino)-1-piperidyl)pentoxy]carbostyril.

COMPOUNDS OF THE INVENTION

The compounds of this invention comprise carbostyril derivatives of Formula I:

wherein:
m is 0, 1, or 2;
n is 0, 1, or 2;
$R^1$ is hydrogen or lower alkyl;
$R^2$ is hydrogen, halogen, hydroxy, lower alkyl, lower alkoxy, aralkoxy, or acyloxy;
$R^3$ is hydrogen, halogen, lower alkyl, or lower alkoxy;
$R^4$ is hydrogen, hydroxy, lower alkyl, or acyloxy, provided that when $R^4$ is hydroxy or acyloxy, m and n are both 1;
$R^5$ is hydrogen or lower alkyl; and
$R^6$ is alkyl, hydroxyalkyl, alkoxyalkyl, or (dialkylamino)alkyl;

and the pharmaceutically acceptable acid addition salts and N-oxides thereof.

The compounds of Formula I where m is 1 are preferred, particularly those where n is 1 and $R^4$ is hydroxy, or where n is 0 and $R^4$ is hydrogen. For both preferred subgenuses it is preferred that $R^3$ and $R^5$ are hydrogen, and further preferred that $R^1$ is hydrogen. Finally, further preferred are the compounds where $R^2$ is hydrogen, lower alkyl or lower alkoxy, and most preferred are those compounds where $R^6$ is lower alkyl. Also preferred are the pharmaceutically acceptable acid addition salts of the foregoing compounds, particularly the hydrochloride salts.

For the subgenus of compounds where m and n are 1, and $R^4$ is hydroxy, it is preferred that $R^1$, $R^3$ and $R^5$ are hydrogen, further preferred that $R^2$ is hydrogen, and most preferred that $R^6$ is lower alkyl (particularly ethyl, butyl, 2-methylpropyl and cyclopropylmethyl, especially 2-methylpropyl).

For the subgenus of compounds where m is 1, n is 0, and $R^4$ is hydrogen, it is preferred that $R^1$, $R^3$ and $R^5$ are hydrogen, further preferred that $R^2$ is lower alkyl or lower alkoxy (especially methoxy), and most preferred that $R^6$ is lower alkyl (particularly ethyl, butyl, 2-methylpropyl and cyclopropylmethyl, especially cyclopropylmethyl).

The compounds of Formula I that are presently most preferred are:

3,4-dihydro-5-[2-hydroxy-3-(4((2-methylpropoxy)carbonylamino)-1-piperidyl)propoxy]carbostyril hydrochloride, and 8-methoxy-3,4-dihydro-5-[2-(4-((cyclopropylmethoxy)carbonylamino)-1-piperidyl)ethoxy]carbostyril hydrochloride.

UTILITY

The compounds of this invention are useful for the treatment of cardiovascular diseases in mammals, particularly humans, including a wide variety of arrhythmias, including supraventricular premature beat, heart block (first and second degree and complete), atrial fibrillation, atrial flutter, atrial tachyarrhythmia of other etiology, atrioventricular nodal or atrioventricular junctional arrhythmias, ventricular premature beats (unifocal and multifocal), torsades de pointes, ventricular tachyarrhythmia, ventricular fibrillation, and to prevent sudden death, particularly after myocardial infarction or in congestive heart failure. In particular, the compounds of the present invention are useful for the treatment of supraventricular arrhythmia, ventricular tachycardia, and junctional re-entry arrhythmia.

The utility of a compound for treating arrhythmia can be assessed in vitro by measuring the ability of the compound to prolong the effective refractory period in guinea-pig papillary muscle as described by Brückner, Schmitz & Scholz (Naunyn-Schmiedeberg's Arch. Pharmacol. (1985) 329, 86–93) using the preparation described by Dumez, Patmore, Ferrandon, Allely & Armstrong (J. Cardiovascular Pharmacol., 1989, 14, 184–193). The in vivo antiarrhythmic activity of a compound may be determined by measuring its ability to prolong the ventricular refractory period and the QTc-interval of the ECG in an anesthetized guinea-pig (see, e.g., Poizot, J. Pharmacol. (Paris) 17 (1986) 712–719).

The compounds of this invention demonstrate antiarrhythmic activity in the above-mentioned tests, the details of which are set out below in Examples 8 and 9.

FORMULATION AND ADMINISTRATION

A second aspect of this invention comprises pharmaceutical compositions useful in the treatment of arrhythmia in mammals. Such compositions contain a therapeutically effective amount of a compound of Formula I or a pharmaceutically acceptable acid addition salt or N-oxide thereof, in admixture with pharmaceutically acceptable excipient(s).

The level of the drug in the formulation can vary from about 0.1 percent weight (% w) to about 95% w of the drug based on the total formulation and about 99.9% w to 5% w excipient. Preferably the drug is present at a level of about 0.1% w to about 80% w.

Useful pharmaceutical excipients for the preparation of the pharmaceutical compositions hereof can be solids or liquids. Thus, the compositions can take the form of tablets, capsules, powders, sustained release formulations, solutions, suspensions, aerosols, and the like.

Liquid excipients can be selected from the various oils, including those of petroleum, animal, vegetable or synthetic origin, for example, peanut oil, soybean oil, mineral oil, sesame oil, and the like. Water, saline, aqueous dextrose, and glycols are preferred liquid carriers, particularly for injectable solutions.

Suitable solid excipients include starch, cellulose, microcrystalline cellulose, talc, glucose, lactose, sucrose, gelatin, povidone, crosscarmellose sodium, magnesium stearate, sodium stearate, glycerol monostearate, sodium chloride, and the like.

Other suitable pharmaceutical excipients and their formulations are described in "Remington's Pharmaceutical Sciences" 16th Edit. 1980, by E. W. Martin.

A third aspect of this invention comprises methods for treating arrhythmia in mammals (particularly humans) which comprise administering a therapeutically effective amount of a compound of Formula I or a pharmaceutically acceptable acid addition salt or N-oxide thereof, or a composition containing it, to the mammalian subject.

In the practice of this method, a therapeutically effective amount of the compound of Formula I or a pharmaceutical composition containing it is administered in any of the usual and acceptable methods known in the art, either singly or in combination with another compound or compounds of the present invention or other pharmaceutical agents. These compounds or compositions can thus be administered orally, systemically (e.g., transdermally, intranasally or by suppository) or parenterally (e.g. intramuscularly, subcutaneously and intravenously), and can be administered either in the form of solid or liquid dosages including tablets, solutions, suspensions, aerosols, and the like, as discussed in more detail above. It is preferred to administer compounds of Formula I orally and parenterally.

The formulation can be administered in a single unit dosage form for continuous treatment or in a single unit dosage form ad libitum when relief of symptoms is specifically required.

In view of the foregoing as well as in consideration of the degree of severity of the condition being treated, age of subject and so forth, all of which factors are determinable by routine experimentation by one skilled in the art, the effective dosage in accordance herewith can vary over a wide range. Generally a therapeutically effective amount ranges from about 0.01 to about 25 mg/kg body weight per day and preferably about 0.05 to about 20 mg/kg body weight per day. In alternative terms, for an average 70 kg adult human subject, a therapeutically effective amount in accordance herewith would be, in preferred embodiments from about 0.7 mg to about 1750 mg per day per subject, and preferably from about 3.5 mg to 1400 mg per day per subject.

PREPARATION OF COMPOUNDS OF THE INVENTION

The compounds of Formula I are prepared as shown below in Reaction Schemes I-V, where Reaction Scheme I shows the preparation of 4-piperidylcarbamate intermediates of Formula 4 and Reaction Scheme II shows the preparation of the compounds of Formula I from those intermediates. Reaction Schemes III, IV and V show the preparation of 3,4-dihydrocarbostyril intermediates of Formula 5.

In the Reaction Schemes, $R^1$, $R^2$, $R^3$, $R^4$, $R^5$, and $R^6$, are as described in the broadest scope of the invention, except as noted. For those compounds in which $R^6$ is lower alkyl, it is convenient to prepare intermediates of Formula 2 directly, following Alternate A of Step 1 of Reaction Scheme I. Intermediates of Formula 2 may also be prepared indirectly, following Alternate B of Step 1 of Reaction Scheme I and passing through intermediates of Formula 3, as described in Preparations 2 and 3 below.

REACTION SCHEME I

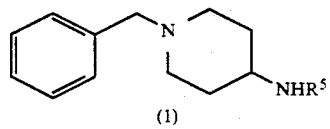

(1)

REACTION SCHEME I
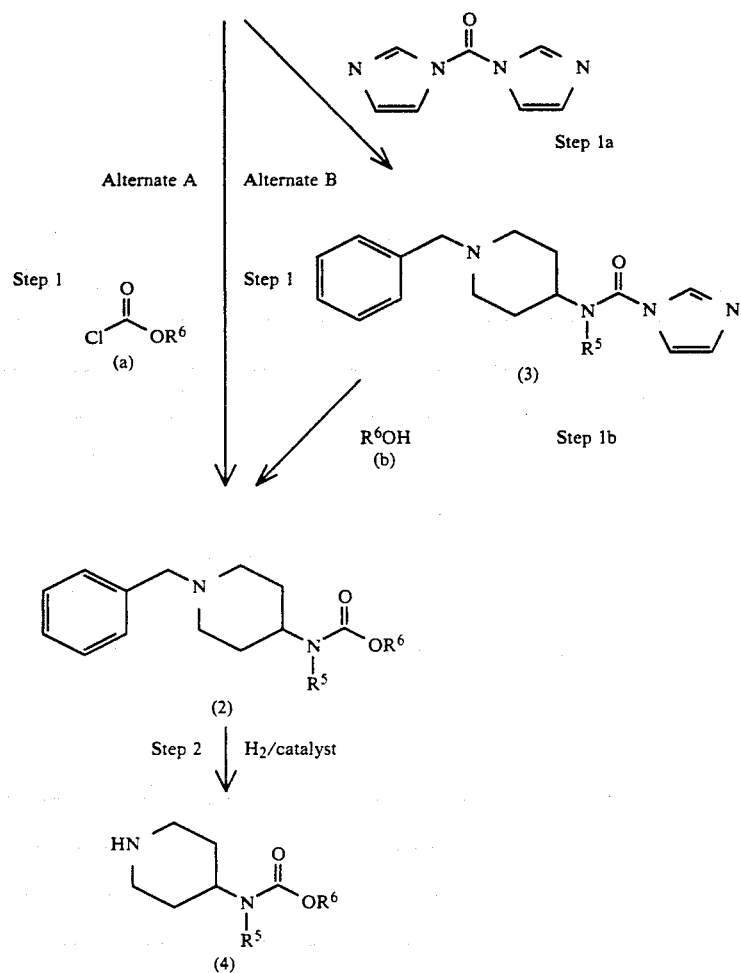
REACTION SCHEME II
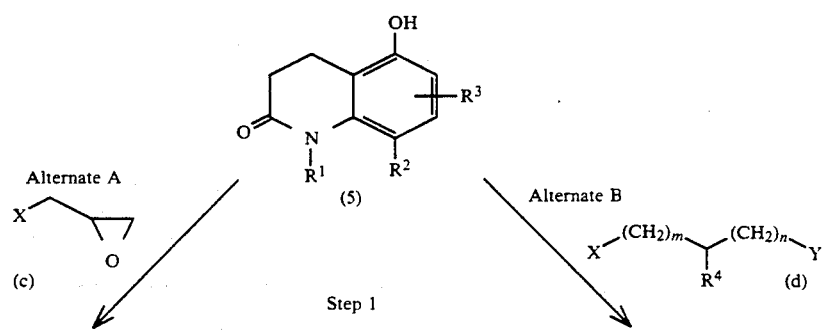

-continued
REACTION SCHEME II
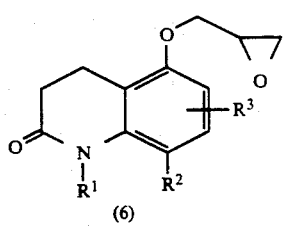
(6)
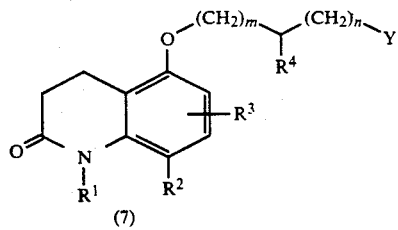
(7)
Step 2
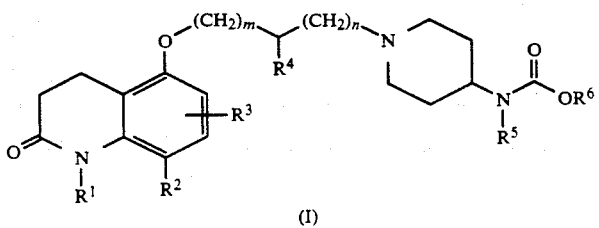
(I)
REACTION SCHEME III
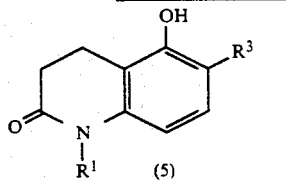
(5)
Step 1 | HCHO + HN(R)(R) (8)
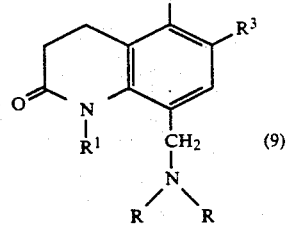
(9)
Step 2 | H₂ Pd(OH)₂/C
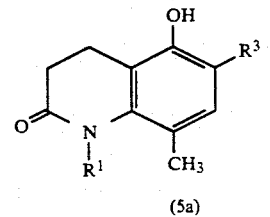
(5a)
REACTION SCHEME IV
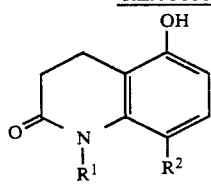
(5)
Step 1 | HCHO H₂N—W (10)
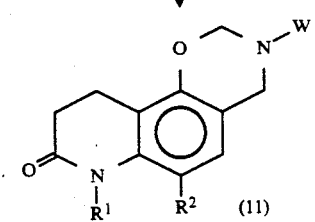
(11)
Step 2 | H₂ Pd(OH)₂/C
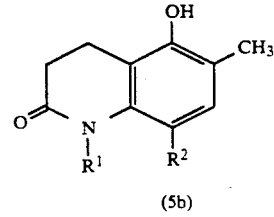
(5b)

REACTION SCHEME V

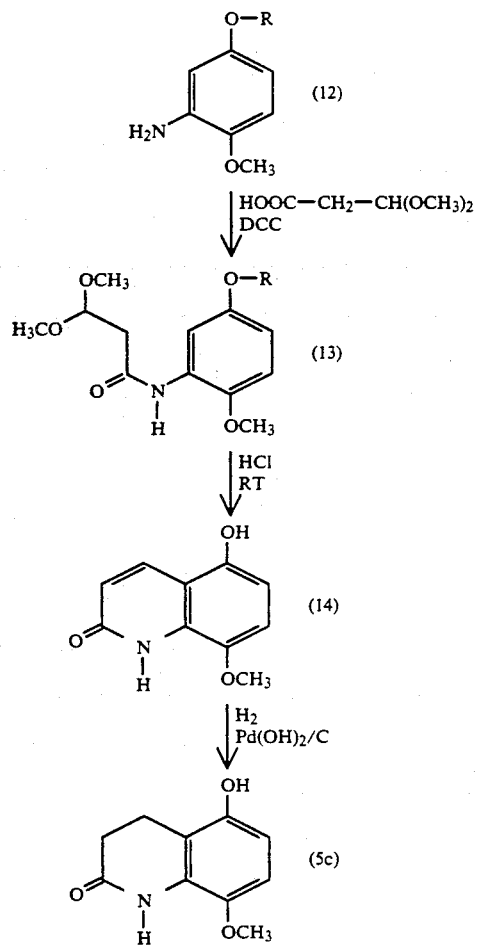

STARTING MATERIALS

The starting materials used in preparation of the compounds of the present invention, including the dihydrocarbostyrils, alkyl chloroformates, carbonyldiimidazole, 4-amino-1-phenylmethylpiperidine, epoxides (glycidyl halides and glycidyl sulfonates), dihalo compounds, and the other reagents, solvents, catalysts and equipment described are typically commercially available or can be prepared by methods known to those skilled in the art.

5-Hydroxy-3,4-dihydrocarbostyrils of Formula 5 may be made as described with reference to Reaction Schemes III to V, or according to methods described in the literature: e.g., 5-hydroxy-3,4-dihydrocarbostyril may be easily prepared according to the method described in J. Org. Chem. 1981, 46, 3719; 5,8-dihydroxy-3,4-dihydrocarbostyril may advantageously be obtained from methods described by Uchida, et al., in *Yakugaku Zasshi*, 96, 571, 1976; and 5-hydroxy-8-phenyl-methoxy-3,4-dihydrocarbostyril may be prepared according to the method described by Tominaga, et al., in *Chem. Pharm. Bull*, 29(8) 2161–65, 1981; and 5-hydroxy-8-bromo and 5-hydroxy-6,8-dichloro-3,4-dihydrocarbostyrils may be synthesized as per methods described in U.S. Pat. No. 4,482,560.

Alkyl chloroformates (e.g., methyl chloroformate, ethyl chloroformate, propyl chloroformate, butyl chloroformate, isobutylchloroformate) are readily available from inter alia Aldrich Chemical Co. (Wisconsin).

Carbonyldiimidazole is commercially available from e.g., Aldrich Chemical Co. (Wisconsin).

4-Amino-1-phenylmethylpiperidine is readily available from e.g., Aldrich Chemical Co. (Wisconsin).

Epihalohydrins (e.g., epibromohydrin, epichlorohydrin) and glycidyl sulfonates (e.g. (2R) or (2S)-glycidyl tosylate) are commercially available from inter alia Aldrich Chemical Co. (Wisconsin).

ω-Dihaloalkanes (e.g., 1,2-dibromoethane, 1,2-dichloroethane, 1,3-dibromo-2-propanol, 1,3-dichloro-2-propanol) are commercially available from e.g., Adrich Chemical Co. (Wisconsin).

PREPARATION OF FORMULA 2

As shown in Reaction Scheme 1, Alternate A, Step 1, a 4-(optionally substituted)amino-1-phenylmethylpiperidine (Formula 1) and a chloroformate (Formula a) are reacted in a suitable inert solvent to give the corresponding substituted carbamic acid ester of Formula 2. The reaction conditions can be generalized as follows: addition temperature: from $-10°$ to $+40°$ C., preferably $-5°$ to $+10°$ C.; reaction time: from 4 to 48 hours, preferably 8 to 24 hours; reaction temperature: from 10° to 100° C., preferably 20° to 40° C.

Similar reactions (the action of a chloroformate on a primary or secondary amine) are well known to persons of ordinary skill in the art, for example as described in Patent Fr. Demande 2,321,890 from SYNTHELABO S.A.

ALTERNATIVE PREPARATION OF FORMULA 2

Preparation of Formula 3

As shown in Reaction Scheme I, Alternate B, Step 1a, a 4-(optionally substituted)amino-1-phenylmethylpiperidine (Formula 1) and carbonyldiimidazole (CDI) are mixed in a polar aprotic solvent, e.g. tetrahydrofuran (THF), dioxane, dimethylformamide or the like, and heated between 20° and 100° C. for approximately 4 to 24 hours. When the reaction is substantially complete, a precipitate forms giving the corresponding 4-imidazolylcarbonylamino-1-phenylmethylpiperidine compound of Formula 3, which is isolated by conventional means.

The condensation between an amine and the carbonyl diimidazole to produce compounds such as Formula 3 is described in H. A. Staab and W. Benz, Ann. der Chem. 648, 72 (1961).

Conversion to Formula 2

As shown in Reaction Scheme I, Alternate B, Step 1b, the imidazolyl derivative of Formula 3 is contacted with an alcohol of Formula b. When $R^6$ of Formula b represents $C_1$ to $C_4$ lower alkyl or lower alkoxyalky, the alcohol can be used in large excess and also serve as the solvent. In the other cases, a polar aprotic solvent (e.g., THF, dioxane), can be used. The recommended temperature range is 10° to 60° C. and the reaction is usually complete after 6 to 24 hours. The corresponding substituted carbamic acid ester of Formula 2 is isolated by conventional means.

PREPARATION OF FORMULA 4

As shown in Reaction Scheme I, Step 2, the protecting group (N-phenylmethyl) of Formula 2 is removed by hydrogenolysis. A compound of Formula 2 is dissolved in an inert solvent (such as methanol, ethanol, propanol, ethylacetate, tetrahydrofuran or acetic acid), and a catalyst (5 to 40% by weight of 5 to 10% palladium or palladium hydroxide on carbon) is added. The hydrogenolysis takes place at 10° to 50° C. under 1 to 3 atmospheres of hydrogen. The reaction is ordinarily complete after 4 to 24 hours. The catalyst is removed by filtration and the desired 4-piperidylcarbamate of Formula 4 is recovered by conventional means, typically giving a yield of about 60 to 100%.

Classical methods for hydrogenolysis are described in "Catalytic Hydrogenation in Organic Synthesis: Procedures and Commentary" by Morris Freifelder; John Wiley and Sons, 1978, p. 112, and, "Protective Groups in Organic Synthesis" by Theodora W. Greene; John Wiley and Sons, 1981, p. 272.

PREPARATION OF FORMULA 6

As shown in Reaction Scheme II, Alternate A, Step 1, a 5-hydroxy-3,4-dihydro-carbostyril of Formula 5 (obtained as discussed above in the starting materials section, or as described below in conjunction with Reaction Schemes III to V) and an epihalohydrin of Formula c are contacted in the presence of a suitable basic compound, preferably an alkali hydroxide (such as sodium hydroxide), in an appropriate inert solvent (e.g., lower alkanol or water). The reactants are used in an equimolar ratio or the epihalohydrin can be up to 10 times the molar quantity of the compound of Formula 5. Reaction temperature ranges from 20° to 100° C., preferably at the reflux temperature of the solvent and reaction is generally complete after 4 to 24 hours. The reaction product, a 5-(2,3-epoxypropoxy)-3,4-dihydrocarbostyril compound of Formula 6, is purified by conventional means, e.g., extractions by an organic solvent, fractional recrystallizations, column chromatography methods, or the like.

The preparation of Formula 6 may be conducted according to the procedure described in U.S. Pat. No. 4,482,560.

PREPARATION OF FORMULA 7

As shown in Reaction Scheme II, Alternate B, Step 1, a 5-hydroxy-3,4-dihydro-carbostyril of Formula 5 (obtained as discussed above, or as described in conjunction with Reaction Schemes III, IV and V below) and 1 to 2 molar equivalents of an ω-dihaloalkane of Formula d are contacted together in the presence of a dehalogenating agent, preferably an alkali hydroxide (such as sodium hydroxide), in an inert solvent at room temperature to 100° C. for 4 to 12 hours. A small quantity of a metal iodide can optionally be added to increase the yield. Isolation and purification of the resulting 5-(haloalkoxy)-3,4-dihydrocarbostyril compound of Formula 7, if required, are achieved by common methods, like extraction, crystallization or column chromatography.

The compounds of Formula 7 can be obtained using known procedures, e.g., as described in JP 5,1133.274 and in U.S. Pat. No. 4,482,560.

PREPARATION OF FORMULA I WHEREIN $R^4$ IS OH

As shown in Reaction Scheme II, Alternate A, Step 2, a 5-(2,3-epoxypropoxy)-3,4-dihydrocarbostyril of Formula 6 is contacted with a secondary amine of Formula 4 in an inert solvent that will dissolve both reactants, for example, a lower alkanol polar solvent (such as methanol or butanol, preferably ethanol or isopropanol). The reaction is generally complete after heating the medium in the range of 40° to 100° C. (preferably at the reflux temperature of the selected solvent) while stirring for about 6 to 24 hours, preferably for 12 to 16 hours. The desired corresponding compound of Formula I (where $R^4$ is hydroxy) is recovered as a free base using conventional means or as an acid addition salt. The compound of Formula I is preferably recovered as a hydrochloride salt by addition of an excess of hydrochloric acid to the cooled reaction medium.

The reaction of a 5-(2,3-epoxypropoxy)-3,4-dihydrocarbostyril and a secondary amine which is analogous to that shown in Formula 4 is described particularly in U.S. Pat. No. 4,482,560 and by K. Nakagawa et al., J. Med. Chem. 1974, vol. 17, No. 5, p. 529–533.

PREPARATION OF FORMULA I WHEREIN $R^4$ IS H OR LOWER ALKYL

As shown in Reaction Scheme II, Alternate B, Step 2, a 5-(haloalkoxy)-3,4-dihydrocarbostyril compound of Formula 7 is contacted with a secondary amine of Formula 4 on an equimolar basis; the medium is kept basic by addition of one molar equivalent of an agent able to capture hydrochloric acid (or "hydrogen halide receptor", e.g., triethylamine, potassium or sodium carbonate, and the like). The reaction takes place in a variety of polar or nonpolar solvents (e.g. tetrahydrofuran, dioxane, toluene, methanol, ethanol, isopropanol). The reaction medium is heated while stirring at 15°–130° C. (preferably at the reflux temperature of the selected solvent) for 6 to 72 hours (preferably 24 to 48 hours). The desired corresponding compound of Formula I (where $R^4$ is hydrogen or lower alkyl) is recovered as a free base using conventional means, and can then be converted into an addition salt by methods known to those of ordinary skill in the art.

The 5-(haloalkoxy)-3,4-dihydrocarbostyrils and secondary amines can be condensed using conventional methods. Such methods are described in: GER. OFFEN. 3.034.237 and U.S. Pat. No. 4,482,560.

ALTERNATE PREPARATION OF FORMULA 5 Where $R^2$ and/or $R^3$ are Methyl

The compounds of Formula 5 where $R^2$ and/or $R^3$ are methyl can be advantageously prepared as described below with reference to Reaction Schemes III and IV.

Adding Methyl at $R^2$

As illustrated in Reaction Scheme III, Step 1, a 5-hydroxy-3,4-dihydrocarbostyril of Formula 5, where $R^1$ is hydrogen or lower alkyl, $R^2$ is hydrogen, and $R^3$ is hydrogen, halo, lower alkyl or lower alkoxy at the 6-position (obtained as described above in the Starting Materials section, or described below with reference to Reaction Scheme IV) is contacted with a large excess of formaldehyde and one to two molar equivalents of a dialkyl amine (Formula 8 where R is lower alkyl) in an aqueous solvent, preferably water. After stirring at room temperature for about 2 to 10 hours, preferably 5 hours, a precipitate forms and is isolated by conventional means, e.g., filtration and washing with cold water) to give the 5-hydroxy-6-(optionally lower alkyl)-8-(dialkylaminomethyl)-3,4-dihydrocarbostyril of Formula 9, which can serve as a Mannich base in subsequent reactions.

As illustrated in Reaction Scheme III, Step 2, a Mannich base of Formula 9 is dissolved in an inert solvent (such as a polar solvent, e.g., a lower alcohol, preferably ethanol) and hydrogenated at elevated temperature (such as about 50° to 75° C., preferably 60° C.) over a palladium hydroxide on carbon catalyst for 12 to 24 hours, preferably about 16 hours. The catalyst is removed (e.g., by filtration) and the compound of Formula 5(a) is isolated by conventional means (e.g., evaporation of the solvent and recrystallization from ethanol).

Adding Methyl at $R^3$

As illustrated in Reaction Scheme IV, Step 1, a 5-hydroxy-3,4-dihydrocarbostyril of Formula 5, where $R^1$ is hydrogen or lower alkyl, $R^2$ is hydrogen, halo, lower alkyl or lower alkoxy, and $R^3$ is hydrogen (obtained as described above in the Starting Materials section or with reference to Reaction Scheme III) is contacted with two to three molar equivalents of formaldehyde and one molar equivalents of a primary amine (Formula 10 where W is alkyl, aryl or cycloalkyl) in an aqueous solvent, preferably water. After stirring at room temperature for about 8 to 16 hours, preferably about 12 hours, a precipitate forms and is isolated by conventional means (e.g., filtration and recrystallization from methanol) to give the oxazine of Formula 11.

As illustrated in Reaction Scheme IV, Step 2, an oxazine of Formula 11 is dissolved in an inert solvent (such as a polar solvent, e.g., a lower alcohol, preferably methanol) and hydrogenated at room temperature or optionally at elevated temperature (such as about 50° to 75° C., preferably at room temperature) over a palladium hydroxide on carbon catalyst for 12 to 24 hours, preferably about 16 hours. The catalyst is removed (e.g., by filtration) and the compound of Formula 5(b) is isolated by conventional means (e.g., evaporation of the solvent and recrystallization from ethanol).

Conversion to Formula I

The compounds of Formulae 5a and 5b can be employed as the compound of Formula 5 in the reactions described with reference to Reaction Scheme II, and thereby be converted to compounds of Formula I wherein $R^2$ and/or $R^3$ are methyl.

SECOND ALTERNATE PREPARATION OF FORMULA 5

The compounds of Formula 5 where $R^1$ and $R^3$ are hydrogen, and $R^2$ is lower alkoxy (particularly methoxy), can be advantageously prepared as described below with reference to Reaction Scheme V.

Preparation of Formula 12

Compounds of Formula 12, where R is phenylmethyl or acetyl are obtained as follows.

Where R is phenylmethyl

4-Phenylmethoxy-phenol in acetic acid is nitrated by contact with a slight molar excess of nitric acid at room temperature, giving 2-nitro-4-phenylmethoxy-phenol.

2-Nitro-4-phenylmethoxy-phenol is methylated by contacting it with a slight molar excess of potassium carbonate and a large molar excess of methyl iodide and tetrabutylammonium bromide (TBAB) in an inert solvent (such as acetone) and refluxed for 8 to 15 hours, preferably 12 hours. After cooling, filtration and evaporation of the solvent, the residue is purified by conventional means to give 2-nitro-4-phenylmethoxyanisole, which in turn is hydrogenated to give the corresponding aniline of Formula 12.

Where R is acetyl 4-methoxy-phenol is acetylated by reflux in a mixture of acetic anhydride and acetic acid for a period of about 10 to 15 hours, preferably about 12 hours. The acetylated derivative is nitrated by contact with a slight molar excess of nitric acid at room temperature, with stirring for about 1 to 4 hours, preferably about 2 hours giving 2-nitro-4-acetyloxy-anisole. The 2-nitro-4-acetyloxy-anisole is hydrogenated to give the corresponding aniline of Formula 12.

Preparation of Formula 13

To a cooled solution of an aniline of Formula 12 and a slight molar excess of 3,3-dimethoxy-propanoic acid (prepared, e.g., by refluxing methyl 3,3-dimethoxy-propanoate and 2N NaOH in water, followed by acidification with hydrochloric acid and isolation by conventional means) in an inert solvent (e.g., methylene chloride), is added 1,3-dicyclohexylcarbodiimide (DCC), followed by stirring at a temperature of about 20° C. to reflux for about 1 to 15 hours, preferably at room temperature for about 4 to 6 hours. The dimethoxy derivative of Formula 13 is isolated by evaporation of the solvent and working up in an alkyl ether, preferably diisopropyl ether.

Preparation of Formula 14

A dimethoxy derivative of Formula 13 is cyclized upon addition to a cooled solution of a strong organic or inorganic acid, such as methanesulfonic acid, hydrochloric acid, hydrobromic acid, sulfuric acid and the like, preferably concentrated hydrochloric acid (about 37%) and stirring at a temperature of about 20° to 80° C., preferably at room temperature for about 30 minutes to about 3 hours, preferably about 1.5 hour. The crude 5-hydroxy-carbostyril of Formula 14 is isolated by filtration of the cooled reaction medium, and purified by trituration in cold water.

Preparation of Formula 5c

A carbostyril of Formula 14 is hydrogenated, e.g., in a mixture of methanol/acetic acid, or preferably in N-methylpyrrolidinone, with a palladium hydroxide catalyst at elevated temperature (e.g., 40° to 80° C.) and under a source of hydrogen for 24 to 48 hours, preferably about 36 hours. The catalyst is removed to give the 3,4-dihydrocarbostyril compound of Formula 5c.

Similarly, by starting with a 4-(lower alkoxy)phenol the corresponding 2-(lower alkoxy)aniline compounds can be prepared and converted to the corresponding 8-(lower alkoxy)-5-hydroxy-3,4-dihydrocarbostyrils.

PREPARATION OF PRODUCTS OF FORMULA I WHEREIN $R^2$ IS OH

Formulae 6 and 7 Wherein $R^2$ is Phenylmethoxy

A compound of Formula 5 (wherein $R^2$ is hydroxy) is contacted with a phenylmethyl halide in the presence of a base to give the corresponding compound of Formula 5 wherein $R^2$ is phenylmethoxy. The resulting 5-hydroxy-8-phenylmethoxy-3,4-dihydrocarbostyril is contacted either with an epihalohydrin or with an ω-dihaloalkane in the presence of a base as described above with reference to Reaction Scheme II, Alternatives A and B, Steps 1, or e.g., following the method described in U.S. Pat. No. 4,210,753.

Formula I Wherein $R^2$ is Phenylmethoxy

A compound of Formula 6 or 7 wherein $R^2$ is phenylmethoxy is condensed with a secondary amine of Formula 4 using the methodology described with respect to Reaction Scheme II, Alternatives A and B, Steps 2, respectively, or e.g., following the method described in Chem. Pharm. Bull, 29(8), 2161–65, 1981.

Formula I Wherein $R^2$ is Hydroxy

Compounds of Formula I wherein $R^2$ is OH are prepared from compounds of Formula I wherein $R^2$ is phenylmethoxy by removing the phenylmethyl protecting group using the methodology described with respect to Reaction Scheme I, Step 2, or according to Chem. Pharm. Bull, 29(8), 2161–65, 1981.

PREPARATION OF COMPOUNDS OF FORMULA I WHERE $R^2$ AND/OR $R^4$ ARE AN ACYLOXY GROUP.

Esterification of one or both of the hydroxy groups ($R^2$ and $R^4$) of compounds of Formula I can be done according to known methods, using selective reactions when monoacylation is desirable. See "Protecting Groups in Organic Synthesis," Theodora W. Greene, John Wiley and Sons, 1981.

Esterification is generally accomplished by heating the compound of Formula I ($R^2$ and/or $R^4$ are OH) with an equivalent or an excess of the appropriate carboxylic acid anhydride, chloride or bromide in a suitable solvent in the presence of a tertiary amine. Temperature is kept at 10°–90° C. for 4–24 hours, preferably at 15°–30° C. for 6–8 hours. The desired ester is then recovered by conventional extraction and purification methods. Examples can be found in U.S. Pat. No. 4,374,835 and the appropriate sections of Morrison and Boyd, supra and Fieser and Fieser, *Reagents for Organic Synthesis*, John Wiley and Sons, Inc., New York, published in 1967. Suitable esters which are prepared include acetates, propionates, butanoates, hexanoates, octanoates, dodecanoates and the like.

PREPARATION OF COMPOUNDS OF FORMULA I AS PURE ENANTIOMERS

From a Racemic Mixture of Formula I

Products of Formula I wherein $R^4$ is not a hydrogen atom exist in two different enantiomeric forms which can be resolved using conventional methods.

One such method consists of contacting a racemic compound of Formula I with a suitable optically active acid e.g. preferably L-pyroglutamic acid in a ratio which may vary from 0.8:1 to 1.4:1, preferably 1:1, in a lower alkanol solvent, at a temperature within approximately 10° C. of the reflux temperature of the solvent, and then allowing the resulting insoluble optically active acid salt of Product I to crystallize from the solution.

The crystalline insoluble optically active acid salt of Product I is then cleaved with a suitable base, preferably with sodium or potassium hydroxide, to produce the (R)(+) enantiomer of Product I.

The (S)(−) enantiomer of Product I can be prepared starting from the remaining mother liquors of the crystallized optically active acid salt of Product I obtained above.

The mother liquors are concentrated under reduced pressure and the residue is treated with aqueous potassium or sodium hydroxide. The aqueous phase is extracted with a suitable organic solvent (preferably methylene chloride or chloroform) which is then worked up by conventional means to recover the crude (S)(−) enantiomer of Product I. Purification is achieved by contacting the crude (S)(−) enantiomer of Product I with D-pyroglutamic acid following the method described above.

From Optically Active Intermediates

Enantiomers of compounds of Formula I wherein $R^4$ is OH can also be prepared by reacting first a compound of Formula 5 with a chiral epihalohydrin according to general conditions described under Reaction Scheme II, Alternate A, then condensing the resulting chiral compound of Formula 6 with a piperidylcarbamate of Formula 4 following the reaction conditions given under Reaction Scheme II, Alternate A, Step 2.

Chiral epihalohydrins are commercially available, e.g. (2R) and (2S)-epichlorohydrins may be obtained from DAISO Co. Ltd. (Japan).

Alternatively, in Reaction Scheme II, Alternate A, epihalohydrins can be replaced by chiral glycidyltosylates which are readily available, e.g. (2R)-and (2S)-glycidyltosylates can be obtained from Aldrich Chemical Co. (Wisconsin).

The reaction between a glycidyltosylate and a 5-hydroxycarbostyril (Formula 5) is carried out in the presence of a suitable base, preferably an alkaline hydride or hydroxide, in an appropriate solvent (e.g. a solvent in which the alkaline salt of Formula 5 is soluble at low temperature). Reaction temperature ranges from 20° to 100° C., preferably 50°–80° C., and reaction is generally complete within 2 to 8 hours. The reaction product is purified by conventional means, e.g. extraction by an organic solvent, fractional recrystallization, column chromatography, or the like.

PREPARATION OF PRODUCTS OF FORMULA I AS ACID ADDITION SALTS

The compounds of Formula I in free base form may be converted to the acid addition salts by treatment with the appropriate organic or inorganic acid, such as, for example, phosphoric, pyruvic, hydrochloric or sulfuric acid and the like. Typically, the free base is dissolved in a polar organic solvent such as ethanol or methanol, and the acid added thereto. The temperature is maintained between about 0° C. and about 100° C. The resulting acid addition salt precipitates spontaneously or may be brought out of solution with a less polar solvent.

The acid addition salts of the compounds of Formula I may be decomposed to the corresponding free base by treatment with a suitable base, such as potassium carbonate or sodium hydroxide, typically in the presence of an aqueous solvent, and at a temperature of between about 0° C. and 100° C. The free base form is isolated by conventional means, such as extraction with an organic solvent.

Salts of the compounds of Formula I may be interchanged by taking advantage of differential solubilities and volatilities, or by treatment with a suitably loaded ion exchange resin. This conversion is carried out at a temperature between about 0° C. and the boiling point of the solvent being used as the medium for the procedure.

In summary, compounds of Formula I are prepared according to the following last steps:

a. contacting a racemic or chiral 5-(2,3-epoxypropoxy)-3,4-dihydrocarbostyril with a 4-piperidylcarbamate to give a compound according to Formula I where $R^4$ is OH; or b. contacting a 5-(haloalkoxy)-3,4-dihydrocarbostyril with a 4-piperidylcarbamate to give a compound according to Formula I where $R^4$ is H or lower alkyl; or c. acylating a compound of Formula I wherein either $R^2$ or $R^4$ is OH, or $R^2$ and $R^4$ are both OH; or d. saponifying a compound of Formula I wherein either $R^2$ or $R^4$ is —O—CO—alkyl, or $R^2$ and $R^4$ are both —O—CO—alkyl; or e. deprotecting a compound of Formula I wherein $R^2$ is aralkoxy; or f. resolving a racemic mixture of stereoisomers of Formula I into pure enantiomers using an appropriate optically active acid; or g. converting a compound of Formula I in free base form to the acid addition salt by treatment with the appropriate organic or inorganic acid; or h. decomposing an acid addition salt of a compound of Formula I to the corresponding free base by treatment with a suitable base or by treatment with a suitably loaded ion exchange resin; or i. interchanging an acid addition salt of a compound of Formula I with another acid addition salt by taking advantage of differential dissociation constants, solubilities or by treatment with a suitably loaded ion exchange resin.

The following preparations and examples are given to enable those skilled in the art to more clearly understand and practice the present invention. They should not be considered as a limitation on the scope of the invention, but merely as being illustrative and representative thereof.

PREPARATIONS

PREPARATION 1

Lower Alkyl (1-Phenylmethyl-4-piperidyl)carbamates

Intermediates of Formula 2

(A) Ethyl (1-phenylmethyl-4-piperidyl)carbamate

Ethyl chloroformate (30 g, 0.276 mol) was added at 0° C. to 4-amino-1-phenylmethylpiperidine (50 g, 0.262 mol) in pyridine (600 mL). After the addition, the mixture was kept at room temperature overnight, and the pyridine was then evaporated. The residue was extracted with methylene chloride; and the resulting solution washed with water, dried over sodium sulfate, and the methylene chloride evaporated to dryness. The residue was dissolved in diisopropyl ether. A white product precipitated, which was isolated by filtration to yield 42.71 g (62%) of ethyl (1-phenylmethyl-4-piperidyl)-carbamate, m.p. 100° C.

(B) Similarly, proceeding as in part A above, but replacing ethyl chloroformate by:
methyl chloroformate,
propyl chloroformate,
isopropyl chloroformate,
butyl chloroformate, and
isobutyl chloroformate, respectively,
the following compounds were prepared:
methyl (1-phenylmethyl-4-piperidyl)carbamate, m.p. 88° C.,
propyl (1-phenylmethyl-4-piperidyl)carbamate, m.p. 92° C.,
isopropyl (1-phenylmethyl-4-piperidyl)carbamate, m.p. 95° C.,
butyl (1-phenylmethyl-4-piperidyl)carbamate, m.p. 94° C., and
isobutyl (1-phenylmethyl-4-piperidyl)carbamate, m.p. 110° C.

(C) Similarly, proceeding as in part A above, but replacing 4-amino-1-phenylmethylpiperidine with a compound of Formula 1 where $R^5$ is lower alkyl, and optionally replacing ethyl chloroformate with a different lower alkyl chloroformate, the following intermediates of Formula 2 are prepared:
methyl N-methyl-(1-phenylmethyl-4-piperidyl)carbamate,
methyl N-ethyl-(1-phenylmethyl-4-piperidyl)carbamate,
methyl N-isobutyl-(1-phenylmethyl-4-piperidyl)carbamate,
ethyl N-methyl-(1-phenylmethyl-4-piperidyl)carbamate,
ethyl N-ethyl-(1-phenylmethyl-4-piperidyl)carbamate,
ethyl N-isobutyl-(1-phenylmethyl-4-piperidyl)carbamate,
propyl N-methyl-(1-phenylmethyl-4-piperidyl)carbamate,
propyl N-ethyl-(1-phenylmethyl-4-piperidyl)carbamate,
propyl N-isobutyl-(1-phenylmethyl-4-piperidyl)carbamate,
isopropyl N-methyl-(1-phenylmethyl-4-piperidyl)carbamate,
isopropyl N-ethyl-(1-phenylmethyl-4-piperidyl)carbamate,
isopropyl N-isobutyl-(1-phenylmethyl-4-piperidyl)carbamate,
butyl N-methyl-(1-phenylmethyl-4-piperidyl)carbamate,
butyl N-ethyl-(1-phenylmethyl-4-piperidyl)carbamate,
butyl N-isobutyl-(1-phenylmethyl-4-piperidyl)carbamate,
isobutyl N-methyl-(1-phenylmethyl-4-piperidyl)carbamate, m.p. 125° C.,
isobutyl N-ethyl-(1-phenylmethyl-4-piperidyl)carbamate, and
isobutyl N-isobutyl-(1-phenylmethyl-4-piperidyl)carbamate, m.p. 133° C.

(D) Other lower alkyl N-($R^5$)-(1-phenylmethyl-4-piperidyl)carbamate intermediates of Formula 2 may be prepared in similar fashion, starting with the appropriate lower alkyl chloroformate and 4-($R^5$)amino-1-phenylmethylpiperidine of Formula 1.

PREPARATION 2

4-Imidazolylcarbonylamino-1-phenylmethylpiperidines

Intermediates of Formula 3

(A) 4-imidazolylcarbonylamino-1-phenylmethylpiperidine

4-Amino-1-phenylmethylpiperidine (57.5 g) was dissolved in tetrahydrofuran (150 mL), and the solution added dropwise over a 30 minute period to a cold solution (0° to 5° C.) of carbonyldiimidazole (50 g) in tetrahydrofuran (500 mL). When the addition was complete, the reaction medium was allowed to return to room temperature (20° C.) and stirred continuously for another 20 hours. The solid which precipitated was filtered and washed with ethyl acetate, giving 50 g of 4-imidazolylcarbonylamino-1-phenylmethylpiperidine, m.p. 156° C. The mother liquors were concentrated by evaporating two-thirds of the solvent, producing an additional 14 g yield of the desired compound. The overall yield of 4-imidazolylcarbonylamino-1-phenylmethylpiperidine was 73%.

(B) Similarly, proceeding as in part A above, but replacing 4-amino-1-phenylmethylpiperidine with a compound of Formula 1 wherein $R^5$ is lower alkyl, the following compounds are prepared:
4-(N-methylimidazolycarbonylamino)-1-phenylmethylpiperidine;
4-(N-ethylimidazolycarbonylamino)-1-phenylmethylpiperidine;
4-(N-isopropylimidazolycarbonylamino)-1-phenylmethylpiperidine; and
4-(N-butylimidazolycarbonylamino)-1-phenylmethylpiperidine.

(C) Other 4-(N-lower alkylimidazolylcarbonylamino)-1-phenylmethylpiperidines may be prepared in similar fashion, starting with the appropriate N-($R^5$)-4-amino-1-phenylmethylpiperidine of Formula 1.

PREPARATION 3

Lower alkyl(1-phenylmethyl-4-piperidyl)carbamates

Intermediates of Formula 2

(A) Cyclopropylmethyl (1-phenylmethyl-4-piperidyl)carbamate

A solution of 4-imidazolylcarbonylamino-1-phenylmethylpiperidine (10 g, 0.035 mol), from Preparation 2, in dioxane (100 mL) was added to cyclopropanemethanol (2.42 g, 0.035 mol), then heated overnight at 80°–100° C. with stirring. The reaction mixture was allowed to return to room temperature and the dioxane evaporated under reduced pressure, and the residue was flash-chromatographed using ethyl acetate/heptane (50:50) as eluent. 9.5 g of cyclopropylmethyl (1-phenylmethyl-4-piperidyl)carbamate, m.p. 70°–72° C., was recovered and used in the next step without further purification.

(B) Similarly, proceeding as in part A above, but replacing the cyclopropylmethanol with other alcohols, the following (1-phenylmethyl-4-piperidyl)carbamates were prepared:
methyl (1-phenylmethyl-4-piperidyl)carbamate, m.p. 88° C.,
ethyl (1-phenylmethyl-4-piperidyl)carbamate, m.p. 100° C.,
propyl (1-phenylmethyl-4-piperidyl)carbamate, m.p. 92° C.,
isopropyl (1-phenylmethyl-4-piperidyl)carbamate, m.p. 95° C.,
butyl (1-phenylmethyl-4-piperidyl)carbamate, m.p. 94° C.,
isobutyl (1-phenylmethyl-4-piperidyl)carbamate, m.p. 100° C.,
tert-butyl (1-phenylmethyl-4-piperidyl)carbamate, oil,
isopentyl (1-phenylmethyl-4-piperidyl)carbamate, m.p. 125° C.,
2,2-dimethylpropyl (1-phenylmethyl-4-piperidyl)carbamate, m.p. 137° C.,
2-methoxyethyl (1-phenylmethyl-4-piperidyl)carbamate, oil,
4-hydroxybutyl (1-phenylmethyl-4-piperidyl)carbamate, oil, and
2-dimethylaminoethyl (1-phenylmethyl-4-piperidyl)carbamate, oil.

(C) Similarly, proceeding as in part A above, but replacing 4-imidazolylcarbonylamino-1-phenylmethylpiperidine with 4-(N-methylimidazolylcarbonylamino)-1-phenylmethylpiperidine or 4-(N-isobutylimidazolylcarbonylamino-1-phenylmethylpiperidine, respectively, there were prepared:
isobutyl N-methyl-(1-phenylmethyl-4-piperidyl)carbamate, m.p. 125° C., and
isobutyl N-isobutyl-(1-phenylmethyl-4-piperidyl)carbamate, m.p. 133° C.

(D) Similarly, proceeding as in part A above, but optionally replacing 4-imidazolylcarbonylamino-1-phenylmethylpiperidine with a compound of Formula 3 where $R^5$ is lower alkyl, and optionally replacing cyclopropanemethanol with another alcohol, the following intermediates of Formula 2 are prepared:
cyclopropylmethyl N-methyl-(1-phenylmethyl-4-piperidyl)carbamate,
cyclopropylmethyl N-butyl-(1-phenylmethyl-4-piperidyl)carbamate,
isobutyl N-ethyl-(1-phenylmethyl-4-piperidyl)carbamate,
ethyl N-propyl-(1-phenylmethyl-4-piperidyl)carbamate, and
methyl N-isopropyl-(1-phenylmethyl-4-piperidyl)carbamate.

(E) Other N-($R^5$)-(1-phenylmethyl-4-piperidyl)carbamate intermediates of Formula 2 may be prepared in similar fashion, starting with the appropriate alcohol and compound of Formula 3.

PREPARATION 4

4-Piperidylcarbamates

Intermediates of Formula 4

(A) 2-methoxyethyl 4-piperidylcarbamate

2-Methoxyethyl (1-phenylmethyl-4-piperidyl)carbamate (9.6 g), prepared according to Preparation 3, was dissolved in ethyl acetate (100 mL). Palladium hydroxide (10% on carbon, 1 g) was added, and the mixture was stirred under hydrogen (1 bar) for 6 hours. The catalyst was removed by filtration, and the solvent evaporated to give 6.5 g of 2-methoxyethyl-4-piperidylcarbamate as an oil, which was used without further purification.

(B) Similarly, proceeding as in part A above, but replacing 2-methoxyethyl (1-phenylmethyl-4-piperidyl)carbamate with other intermediates of Formula 2, the following 4-piperidylcarbamates were prepared:
methyl 4-piperidylcarbamate, m.p. 72° C.,
ethyl 4-piperidylcarbamate, m.p. 84° C.,
propyl 4-piperidylcarbamate, m.p. 76° C.,
isopropyl 4-piperidylcarbamate, m.p. 90° C.,
butyl 4-piperidylcarbamate, m.p. 80° C.,
isobutyl 4-piperidylcarbamate, m.p. 106° C.,
tert-butyl 4-piperidylcarbamate, m.p. 145° C.,
isopentyl 4-piperidylcarbamate, m.p. 112° C.;
2,2-dimethylpropyl 4-piperidylcarbamate, m.p. 145° C.,
cyclopropylmethyl 4-piperidylcarbamate, m.p. 125° C.,
cyclopentylmethyl 4-piperidylcarbamate, m.p. 120° C.,
(4-hydroxybutyl) 4-piperidylcarbamate, oil,
diethylaminoethyl 4-piperidylcarbamate, oil,
(2-hydroxy-2-methylpropyl) 4-piperidylcarbamate, m.p. 142° C., isobutyl N-methyl-4-piperidylcarbamate, m.p. 118° C., and
isobutyl N-isobutyl-4-piperidylcarbamate, m.p. 129° C.

(C) Other 4-piperidylcarbamates of Formula 4 may be prepared in similar fashion, starting with the appropriate 1-phenylmethyl intermediate of Formula 2.

PREPARATION 5

5-(2,3-Epoxypropoxy)-3,4-dihydrocarbostyrils

Intermediates of Formula 6

(A) 8-Phenylmethoxy-5-(2,3-epoxypropoxy)-3,4-dihydrocarbostyril

8-Phenylmethoxy-3,4-dihydro-5-hydroxycarbostyril (32.5 g) was dissolved in ethanol (300 mL). Potassium carbonate (25 g) and epichlorohydrin (45 g) were added to the solution, and the mixture heated under reflux for four hours. After cooling, the ethanol was evaporated and water added. The aqueous solution was then extracted with methylene chloride, the resulting solution was washed with water, dried over sodium sulfate and the methylene chloride was evaporated under reduced pressure. The residue was worked up with diisopropyl ether (10 mL), yielding 35 g of 8-phenylmethoxy-5-(2,3-epoxypropoxy)-3,4-dihydrocarbostyril, m.p. 106°–108° C.

(B) Similarly, proceeding as in part A above, but replacing the 8-phenylmethoxy-3,4-dihydro-5-hydroxycarbostyril with:
3,4-dihydro-5-hydroxycarbostyril,
3,4-dihydro-5-hydroxy-1-methylcarbostyril,
8-bromo-3,4-dihydro-5-hydroxycarbostyril,
8-chloro-3,4-dihydro-5-hydroxycarbostyril,
8-fluoro-3,4-dihydro-5-hydroxycarbostyril,
3,4-dihydro-5-hydroxy-8-methylcarbostyril,
3,4-dihydro-5-hydroxy-8-methoxycarbostyril, and
3,4-dihydro-5-hydroxycarbostyril N-oxide,
respectively, the following intermediates of Formula 6 were prepared:
5-(2,3-epoxypropoxy)-3,4-dihydrocarbostyril, m.p. 172°–173° C.,
5-(2,3-epoxypropoxy)-3,4-dihydro-1-methylcarbostyril, m.p. 76° C.,
8-bromo-5-(2,3-epoxypropoxy)-3,4-dihydrocarbostyril, m.p. 220°–222° C.,
8-chloro-5-(2,3-epoxypropoxy)-3,4-dihydrocarbostyril, m.p. 258°–260° C.,
5-(2,3-epoxypropoxy)-8-fluoro-3,4-dihydrocarbostyril,
5-(2,3-epoxypropoxy)-3,4-dihydro-8-methylcarbostyril, m.p. 180° C.,
5-(2,3-epoxypropoxy)-3,4-dihydro-8-methoxycarbostyril, m.p. 196°–198° C., and
5-(2,3-epoxypropoxy)-3,4-dihydrocarbostyril N-oxide.

(C) Other 5-(2,3-epoxypropoxy)-3,4-dihydrocarbostyrils of Formula 6 may be prepared in similar fashion, starting with the appropriate 3,4-dihydro-5-hydroxycarbostyril and either epichlorohydrin or another epihalohydrin.

PREPARATION 6

5-(ω-Haloalkoxy)-3,4-dihydrocarbostyrils

Intermediates of Formula 7

(A) 5-(2-chloroethoxy)-3,4-dihydrocarbostyril

Potassium hydroxide (20 g) was added to a solution of 3,4-dihydro-5-hydroxycarbostyril (32.5 g) in propanol (250 mL), and stirred at 50°–60° C. until complete dissolution. 1-bromo-2-chloroethane (30 g) was then added, and the mixture heated at reflux temperature for 15 hours. After cooling, the reaction mixture was poured into aqueous sodium hydroxide (2N, 500 mL). The crude product thus formed was isolated by filtration, then recrystallized from diisopropyl ether to yield 31 g of pure 5-(2-chloroethoxy)-3,4-dihydrocarbostyril.

(B) Similarly, proceeding as in part A above, but replacing 3,4-dihydro-5-hydroxycarbostyril with another compound of Formula 5, the following compounds of Formula 7 are prepared:
8-chloro-5-(2-chloroethoxy)-3,4-dihydrocarbostyril,
5-(2-chloroethoxy)-3,4-dihydro-8-methylcarbostyril, and
5-(2-chloroethoxy)-3,4-dihydro-8-methoxycarbostyril.

(C) Similarly, proceeding as in part A above, but replacing 1-bromo-2-chloroethane by:
1-bromo-2-chloropropane,
1-bromo-3-chloropropane,
1-bromo-4-chlorobutane,
1-bromo-5-chloropentane,
1-bromo-3-chloro-2-methylpropane, and
2-bromo-1-chloropropane, respectively,
and replacing 3,4-dihydro-5-hydroxycarbostyril with an appropriate compound of Formula 5, there are obtained:
5-(2-chloropropoxy)-3,4-dihydrocarbostyril,
5-(3-chloropropoxy)-3,4-dihydrocarbostyril,
5-(4-chlorobutoxy)-3,4-dihydrocarbostyril,
5-(5-chloropentoxy)-3,4-dihydrocarbostyril,
5-(3-chloro-2-methylpropoxy)-3,4-dihydrocarbostyril, and
5-(2-chloro-1-methylethoxy)-3,4-dihydrocarbostyril.

(D) Similarly, proceeding as in part A above, but replacing 3,4-dihydro-5-hydroxycarbostyril with another compound of formula 5 and 1-bromo-2-chloroethane with another bromochloroalkane, the following compounds of Formula 7 are prepared:
5-(2-chloroethoxy)-3,4-dihydro-1-methylcarbostyril,
8-phenylmethoxy-5-(2-chloroethoxy)-3,4-dihydrocarbostyril,
8-chloro-5-(3-chloropropoxy)-3,4-dihydrocarbostyril,
5-(2-chloro-1-methylethoxy)-3,4-dihydro-8-methylcarbostyril, and
5-(2-chloroethoxy)-3,4-dihydrocarbostyril N-oxide.

PREPARATION 7

8-(dialkylaminomethyl)-3,4-dihydro-5-hydroxycarbostyrils

Intermediates of Formula 9

(A) 8-diethylaminomethyl-3,4-dihydro-5-hydroxycarbostyril

To a stirred suspension of 3,4-dihydro-5-hydroxycarbostyril (30 g, 184 mM) in water (300 mL) was added diethylamine (14 g, 191 mM) followed by a 36% solution of formaldehyde in water (300 mL). The mixture was stirred for 5 hours and the resulting precipitate was filtered and washed with ice-water (50 mL) to give 8-diethylaminomethyl-3,4-dihydro-5-hydroxycarbostyril.

(B) Similarly, proceeding as in part A above, but replacing 3,4-dihydro-5-hydroxycarbostyril with 3,4-dihydro-5-hydroxy-6-methylcarbostyril, there was obtained 8-diethylaminomethyl-3,4-dihydro-5-hydroxy-6-methylcarbostyril.

PREPARATION 8

Intermediates of Formula 5a (A) 3,4-dihydro-5-hydroxy-8-methylcarbostyril

8-Diethylaminomethyl-3,4-dihydro-5-hydroxycarbostyril from Preparation 7, as the crude wet product without further purification was dissolved in ethanol (500 mL) and hydrogenated at 60° C. over 10%-Pd(OH)$_2$/C (1 g) for 16 hours. The catalyst was removed by filtration, the solvent was evaporated and the crude product recrystallized from ethanol to yield 15.2 g (47%) of 3,4-dihydro-5-hydroxy-8-methylcarbostyril as a white solid, m.p. 186°-187° C.

(B) Similarly, proceeding as in part A above, but replacing 8-diethylaminomethyl-3,4-dihydro-5-hydroxycarbostyril with 8-diethylaminomethyl-3,4-dihydro-5-hydroxy-6-methylcarbostyril, there was obtained 3,4-dihydro-5-hydroxy-6,8-dimethylcarbostyril, m.p. 212° C.

PREPARATION 9

(1,3)oxazino(6,5f)-3,4,7,8,9,10-hexahydrocarbostyrils

Intermediates of Formula 10

(A) To a solution of 3,4-dihydro-5-hydroxycarbostyril (15 g, 92 mM) in methanol (500 mL) was added cyclohexylamine (10.5 g, 92 mM) and a 36% solution of formaldehyde in water (50 mL). The mixture was stirred for at room temperature overnight, and the resulting precipitate was filtered and recrystallized from methanol to give (1,3)oxazino(6,5f)-3,4,7,8,9,10-hexahydrocarbostyril as a white solid, m.p. 214°-215° C.

(B) Similarly, proceeding as in part A above, but replacing 3,4-dihydro-5-hydroxycarbostyril with 3,4-dihydro-5-hydroxy-8-methylcarbostyril, there was obtained (1,3)oxazino(6,5f)-3,4,7,8,9,10-hexahydro-8-methylcarbostyril, m.p. 138°-140° C.

PREPARATION 10

Intermediates of Formula 5b (A) 3,4-dihydro-5-hydroxy-6-methylcarbostyril (1,3)Oxazino(6,5f)-3,4,7,8,9,10-hexahydrocarbostyril from Preparation 9 (10 g, 35 mM) was dissolved in methanol (150 mL) and hydrogenated at 60° C. over 10%-Pd(OH)$_2$/C (0.5 g) overnight. The catalyst was removed by filtration, the solvent was evaporated and the crude product recrystallized from ethanol to yield 5.2 g (84%) of 3,4-dihydro-5-hydroxy-6-methylcarbostyril as a white solid, m.p. 181°-182° C.

(B) Similarly, proceeding as in part A above, but replacing (1,3)oxazino(6,5f)-3,4,7,8,9,10-hexahydrocarbostyril with (1,3)oxazino(6,5f)-3,4,7,8,9,10-hexahydro-8-methylcarbostyril, there was obtained 3,4-dihydro-5-hydroxy-6,8-dimethylcarbostyril, m.p. 212° C.

PREPARATION 11

Intermediates of Formula 12 where R is Acetyl

A. One mole of 4-methoxy-phenol in a mixture of 300 ml acetic anhydride and 300 ml acetic acid was refluxed for 12 hours. After cooling, 54 ml of nitric acid (1.3 equivalents, fuming nitric acid, d=1.52) was added dropwise at room temperature. The temperature rose to about 70° C. and nitrous vapors appeared. After completion of the addition the mixture was left under stirring for 2 hours to give 4-methoxy-3-nitrophenyl acetate as a precipitate. Isopropyl ether (300 ml) was added and the mixture was cooled to 0° C. The precipitated material was collected and dried, giving 190 g (yield=90%), m.p. 116° C.

B. 4-Methoxy-3-nitrophenyl acetate (56 g) was added to 400 ml of ethyl acetate with 2.5 g of palladium hydroxide at 20% and stirred under hydrogen for 4 hours. After filtration through Celite the solvent was evaporated under reduced pressure and the residue triturated with a small amount of heptane affording 46.7 g (Yield=97.4%, m.p. 81° C.) of 5-acetoxy-2-methoxyaniline.

PREPARATION 12

Intermediates of Formula 12 where R is Phenylmethyl

A. To 20 g (0.1 mole) of 4-phenylmethoxy-phenol in 200 ml acetic acid were added, dropwise at room temperature, 7.26 ml of nitric acid (d=1.4, 0.105 mole). 2 Hours after completion of the addition the reaction medium was poured onto cold water and extracted twice with 250 ml of methylene chloride. The organic phase was washed twice with 200 ml of water and dried over sodium sulfate. Then the solvent was evaporated and the residue flash chromatographed using ethyl acetate/heptane 30/70 as eluting solvent to give 17.3 g (Yield=70.6%) of 2-nitro-4-phenylmethoxy-phenol.

B. With 82 g (0.335 mole) of 2-nitro-4-phenylmethoxy-phenol, 46 g (0.035 mole) of K$_2$CO$_3$, 83 ml (1.34 moles) of methyl iodide and 2 g of TBAB in 400 ml of acetone were refluxed for 12 hours. The cooled solution was filtered and evaporated. The residue was taken up with methylene chloride, washed with water then dried on sodium sulfate. Evaporation of the solvent gave 73 g (Yield=85%) of 2-nitro-4-phenylmethoxy-anisole.

C. 2-Nitro-4-phenylmethoxy-anisole (73 g) and 1.3 g of platinium oxide in 600 ml of methanol were hydrogenated at room temperature. The catalyst was filtered on Celite and the methanol evaporated. The residue was dissolved in methylene chloride and washed with dilute sodium hydroxide then water. Evaporation of the solvent gave 49.35 g (Yield=76%) of 2-methoxy-5-phenylmethoxy-aniline.

PREPARATION 13

50 g (0.33 mol.) of Methyl 3,3-dimethoxy-propanoate in 200 ml of 2N NaOH solution in water were refluxed 2 hours. After cooling the solution was acidified with hydrochloric acid then extracted two times with 200 ml of CH$_2$Cl$_2$. The extracts were dried on sodium sulfate and evaporated to leave 35 g (Yield=78%) of 3,3-dimethoxy-propanoic acid as an oil.

PREPARATION 14

A. To a cooled solution (0° C.) of 2-methoxy-5-acetyloxy-aniline (5 g, 0.0276 mole), 3,3-dimethoxy-propanoic acid (5 g, 0.0373 mole) in 75 ml of methylene chloride was added DCC (5.7 g, 0.0276 mole) in 20 ml of methylene chloride. After completion of the addition, the solution was stirred for a further 4 hours. The reaction medium was concentrated to 25 ml, diluted with 200 ml of isopropyl ether, cooled to 5° C. and the resulting precipitate was isolated by filtration, giving N-(3,3-dimethoxypropanoyl)-2-methoxy-5-acetoxy-aniline 7.7 g (Yield=95%).

B. To a cooled solution of hydrochloric acid (37%, 40 ml) were added 4 g of the dimethoxy derivative obtained in part A above. After completion of the addition the solution was stirred at room temperature for a further 1.5 hours, at which time a precipitate formed and was filtered and taken up in 15 ml of water, to give 5-hydroxy-8-methoxycarbostyril, 2.2 g (Yield=85.5%, m.p. 236° C.).

C. 5-Hydroxy-8-methoxycarbostyril (12.5 g) in 200 ml of N-methylpyrrolidinone with 500 mg of palladium hydroxide (20%) were hydrogenated at 50° C. under 1,2 bar hydrogen. The catalyst was removed by filtration through Celite and the solvent evaporated to give 12.4 g of 5-hydroxy-8-methoxy-3,4-dihydrocarbostyril (mp=190° C.).

D. By starting with the 4-phenylmethyl derivative obtained in Preparation 12, and following steps A, B and C above, 5-hydroxy-8-methoxy-3,4-dihydrocarbostyril is likewise obtained.

EXAMPLES

EXAMPLE 1

3,4-Dihydro-5-[2-hydroxy-3-(4-$R^6$O-carbonylamino)-1-piperidyl)propoxy]carbostyrils Compounds of Formula I where m=n=1 and $R^4$=OH (A) 3,4-dihydro-5-[2-hydroxy-3-(4-(ethoxycarbonylamino)-1-piperidyl)propoxy]carbostyril (A compound of Formula I where m=n=1, $R^1=R^2=R^3=R^5$=H, $R^4$=OH, and $R^6=C_2H_5$ Ethyl 4-piperidylcarbamate (2 g), from Preparation 4, and 5-(2,3-epoxypropoxy)-3,4-dihydrocarbostyril (2.54 g), from Preparation 5, were dissolved in ethanol (50 mL) and the resulting solution was heated under reflux for 6 hours and then cooled to room temperature. Concentrated hydrochloric acid (1 mL) was added. A white product precipitated, which was collected by filtration. The crude product was recrystallized from ethanol to yield 2.8 g (56.5%) of 3,4-dihydro-5-[2-hydroxy-3-(4-(ethoxycarbonylamino)-1-piperidyl)propoxy]carbostyril hydrochloride, m.p. 232°-234° C. (dec.).

(B) Proceeding as in part A above, but replacing ethyl 4-piperidylycarbamate with isopropyl 4-piperidylcarbamate, there was obtained 3,4-dihydro-5-[2-hydroxy-3-(4-((2-methylpropoxy)carbonylamino)-1-piperidyl)propoxy]carbostyril hydrochloride, m.p. 150° C.

(C) Similarly, proceeding as in part A above, but replacing ethyl 4-piperidylcarbamate with a corresponding compound of Formula 4 and replacing 5-(2,3-epoxypropoxy)-3,4-dihydrocarbostyril with a corresponding compound of Formula 6, the following compounds of Formula I were prepared:

3,4-dihydro-5-[2-hydroxy-3-(4-(methoxycarbonylamino)-1-piperidyl)propoxy]carbostyril hydrochloride, m.p. 250° C.;

3,4-dihydro-5-[2-hydroxy-3-(4-(propoxycarbonylamino)-1-piperidyl)propoxy]carbostyril hydrochloride, m.p. 236° C.;

3,4-dihydro-5-[2-hydroxy-3-(4-butoxycarbonylamino)-1-piperidyl)propoxy]carbostyril hydrochloride, m.p. 252° C.;

3,4-dihydro-5-[2-hydroxy-3-(4-isobutoxycarbonylamino)-1-piperidyl)propoxy]carbostyril hydrochloride, m.p. 240° C.;

3,4-dihydro-5-[2-hydroxy-3-(4-(tert-butoxycarbonylamino)-1-piperidyl)propoxy]carbostyril hydrochloride, m.p. 138° C.;

3,4-dihydro-5-[2-hydroxy-3-(4-(isopentoxycarbonylamino)-1-piperidyl)propoxy]carbostyril hydrochloride, m.p. 220° C.;

3,4-dihydro-5-[2-hydroxy-3-(4-((2,2-dimethylpropoxy)-carbonylamino)-1-piperidyl)propoxy]carbostyril hydrochloride, m.p. 170° C.;

3,4-dihydro-5-[2-hydroxy-3-(4-((cyclopropylmethoxy)-carbonylamino)-1-piperidyl)propoxy]carbostyril hydrochloride, m.p. 250° C.;

3,4-dihydro-5-[2-hydroxy-3-(4-((cyclopentylmethoxy)-carbonylamino)-1-piperidyl)propoxy]carbostyril hydrochloride, m.p. 240° C.;

3,4-dihydro-5-[2-hydroxy-3-(4-((4-hydroxy-n-butoxy)-carbonylamino)-1-piperidyl)propoxy]carbostyril hydrochloride, m.p. 206° C.;

3,4-dihydro-5-[2-hydroxy-3-(4-((diethylaminoethoxy)-carbonylamino)-1-piperidyl)propoxy]carbostyril hydrochloride, m.p. 160° C.;

3,4-dihydro-5-[2-hydroxy-3-(4-((2-hydroxy-2-methylpropoxy)carbonylamino)-1-piperidyl)propoxy]carbostyril hydrochloride, m.p. 210° C.;

3,4-dihydro-5-[2-hydroxy-3-(4-(isobutoxycarbonyl-N-methylamino)-1-piperidyl)propoxy]carbostyril hydrochloride, m.p. 206° C.;

1-methyl-3,4-dihydro-5-[2-hydroxy-3-(4-(isobutoxycarbonylamino)-1-piperidyl)propoxy]carbostyril hydrochloride, m.p. 208° C.;

8-benzyloxy-3,4-dihydro-5-[2-hydroxy-3-(4-(isobutoxycarbonylamino)-1-piperidyl)propoxy]carbostyril hydrochloride, m.p. 196° C.;

3,4-dihydro-5-[2-hydroxy-3-(4-((2-methoxyethoxy)carbonylamino)-1-piperidyl)propoxy]carbostyril hydrochloride, m.p. 230° C.;

3,4-dihydro-5-[2-hydroxy-3-(4-(isobutoxycarbonyl-N-isobutylamino)-1-piperidyl)propoxy]carbostyril hydrochloride, m.p. 128°-130° C.;

8-methoxy-3,4-dihydro-5-[2-hydroxy-3-(4-(isobutoxycarbonylamino)-1-piperidyl)propoxy]carbostyril hydrochloride, m.p. 218° C.;

8-methoxy-3,4-dihydro-5-[2-hydroxy-3-(4-((cyclopropylmethoxy)carbonylamino)-1-piperidyl)propoxy]carbostyril hydrochloride, m.p. 220° C.;

8-methyl-3,4-dihydro-5-[2-hydroxy-3-(4-(isobutoxycarbonylamino)-1-piperidyl)propoxy]carbostyril hydrochloride, m.p. 202° C.; and 8-methyl-3,4-dihydro-5-[2-hydroxy-3-(4-((cyclopropylmethoxy)carbonylamino)-1-piperidyl]carbostyril hydrochloride, m.p. 205° C.

(D) Similarly, proceeding as in part A above, but optionally replacing ethyl 4-piperidylcarbamate with a compound of Formula 4 wherein $R^5$ and $R^6$ are as defined above, and optionally replacing 5-(2,3-epoxypropoxy)-3,4-dihydrocarbostyril with a compound of Formula 6 wherein $R^1$, $R^2$ and $R^3$ are as defined above, the following compounds of Formula I are prepared:

3,4-dihydro-5-[2-hydroxy-3-(4-(isobutoxycarbonylamino)-1-piperidyl)propoxy]carbostyril N-oxide;

3,4-dihydro-5-[2-hydroxy-3-(4-((cyclopropylmethoxy)-carbonylamino)-1-piperidyl)propoxy]carbostyril N-oxide;

6-methyl-3,4-dihydro-5-[2-hydroxy-3-(4-(isobutoxycarbonylamino)-1-piperidyl)propoxy]carbostyril;

6,8-dimethyl-3,4-dihydro-5-[2-hydroxy-3-(4-isobutoxycarbonylamino)-1-piperidyl)propoxy]carbostyril;

6,8-dibromo-3,4-dihydro-5-[2-hydroxy-3-(4-(isobutoxycarbonylamino)-1-piperidyl)propoxy]carbostyril;

8-chloro-3,4-dihydro-5-[2-hydroxy-3-(4-(isobutoxycarbonylamino)-1-piperidyl)propoxy]carbostyril; and 8-fluoro-3,4-dihydro-5-[2-hydroxy-3-(4-isobutoxycarbonylamino)-1-piperidyl)propoxy]carbostyril.

EXAMPLE 2

3,4-Dihydro-5-[ω-(1-piperidyl)alkoxy]carbostyrils

Compounds of Formula I where R4 is H or lower alkyl (A) 3,4-Dihydro-5-[3-(4-(isobutoxycarbonylamino)-1-piperidyl)propoxy]carbostyril (A compound of formula I where m=n=1, $R^1=R^2=R^3=R^4=R^5=H$, and $R^6$=isobutyl 5-(3-chloropropoxy)-3,4-dihydrocarbostyril (2.5 g), from Preparation 6, and isobutyl 4-piperidylcarbamate (2 g), from Preparation 4, were dissolved in tetrahydrofuran (50 mL) containing triethylamine (1.5 mL). The reaction medium was heated for 48 hours under reflux, and the solvent was then removed by evaporation. The residue was dissolved in chloroform (100 mL), and the solution washed with water (2×50 mL), dried over sodium sulfate, and the solvent evaporated. Flash chromatography of the residue, using ethyl acetate/methanol (95:5) as eluent, afforded 0.64 g (15% yield) of the title compound, m.p. 195° C.

The hydrochloride addition salt was formed by treating the free base (0.5 g) with ethanolic hydrochloric acid (6N, 5 mL), then diluting the solution to 100 mL by addition of diethyl ether. 3,4-Dihydro-5-[3-(4-(2-methylpropoxy)carbonylamino-1-piperidyl)propoxy]carbostyril hydrochloride (0.52 g), m.p. 220° C. (dec.), was obtained by filtration.

(B) Proceeding as in part A above, but replacing isobutyl 4-piperidylcarbamate with cyclopropylmethyl 4-piperidylcarbamate, and replacing 5-(3-chloropropoxy)-3,4-dihydrocarbostyril with 5-(2-chloroethoxy)-3,4-dihydro-8-methoxycarbostyril there was obtained 8-methoxy-3,4-dihydro-5-[2-(4-((cyclopropylmethoxy)-carbonylamino)-1-piperidyl)ethoxy]carbostyril hydrochloride, m.p. 218°-220° C.

(C) Similarly, proceeding as in part A above, but replacing 5-(3-chloropropoxy)-3,4-dihydrocarbostyril with another compound of Formula 7 and replacing isobutyl 4-piperidylcarbamate with another compound of Formula 4, the following compounds were prepared:
3,4-dihydro-5-[2-(4-(isobutoxycarbonylamino)-1-piperidyl)ethoxy]carbostyril hydrochloride, m.p. 230° C.;
3,4-dihydro-5-[2-(4-((cyclopropylmethoxy)carbonylamino)-1-piperidyl)ethoxy]carbostyril hydrochloride, m.p. 169°-171° C.;
3,4-dihydro-5-[3-(4-((cyclopropylmethoxy)carbonylamino)-1-piperidyl)propoxy]carbostyril hydrochloride, m.p. 223°-225° C.;
3,4-dihydro-5-[2-methyl-2-(4-((cyclopropylmethoxy)carbonylamino)-1-piperidyl)ethoxy]carbostyril hydrochloride, m.p. 225°-227° C.;
8-chloro-3,4-dihydro-5-[2-(4-((cyclopropylmethoxy)carbonylamino)-1-piperidyl)ethoxy]carbostyril hydrochloride, m.p. 215°-217° C.;
8-methyl-3,4-dihydro-5-[2-(4-((cyclopropylmethoxy)carbonylamino)-1-piperidyl)ethoxy]carbostyril hydrochloride, m.p. 185°-187° C.; and
6-methyl-3,4-dihydro-5-[2-(4-((cyclopropymethoxy)carbonylamino)-1-piperidyl)ethoxy]carbostyril hydrochloride, m.p. 168°-170° C.;
8-methoxy-6-methyl-3,4-dihydro-5-[2-(4-((cyclopropylmethoxy)carbonylamino)-1-piperidyl)ethoxy]carbostyril hydrochloride, m.p. 137°-140° C.;
6,8-dimethyl-3,4-dihydro-5-[2-(4-((cyclopropylmethoxy)carbonylamino)-1-piperidyl)ethoxy]carbostyril hydrochloride, m.p. 163°-165° C.; and
8-methoxy-3,4-dihydro-5-[2-(4-((isobutoxycarbonylamino)-1-piperidyl)ethoxy]carbostyril hydrochloride, m.p. 224°-226° C.

(D) Similarly, proceeding as in part A above, but optionally replacing 5-(3-chloropropoxy)-3,4-dihydrocarbostyril with another compound of Formula 7, and optionally replacing isobutyl 4-piperidylcarbamate with another compound of Formula 4, the following compounds are prepared:
3,4-dihydro-5-[4-(4-(isobutoxycarbonylamino)-1-piperidyl)butoxy]carbostyril;
3,4-dihydro-5-[5-(4-(isobutoxycarbonylamino)-1-piperidyl)pentoxy]carbostyril;
3,4-dihydro-5-[1-methyl-2-(4-isobutoxycarbonylamino)-1-piperidyl)ethoxy]carbostyril;
3,4-dihydro-5-[3-(4-((cyclopropylmethoxy)carbonylamino)-1-piperidyl)propoxy]carbostyril;
8-chloro-3,4-dihydro-5-[5-(4-((cyclopropylmethoxy)-carbonylamino)-1-piperidyl)pentoxy]carbostyril;
1-methyl-3,4-dihydro-5-[3-(4-(isobutoxycarbonylamino)-1-piperidyl)propoxy]carbostyril; and
8-phenylmethoxy-3,4-dihydro-5-[2-(4-((cyclopropylmethoxy)carbonylamino)-1-piperidyl)ethoxy]carbostyril.

EXAMPLE 3

Compounds of Formula I wherein $R^2$ is Hydroxy (A) 8-Phenylmethoxy-3,4-dihydro-5-[2-hydroxy-3-(4-(isobutoxycarbonylamino)-1-piperidyl)propoxy]carbostyril 5-(2,3-epoxypropoxy)-8-phenylmethoxy-3,4-dihydrocarbostyril (130 mg) was dissolved in isopropanol (10 mL) and isobutyl 4-piperidylcarbamate (80 mg) was added. The mixture was then heated under reflux for 20 hours with stirring. After completion of the reaction, the isopropanol was evaporated under reduced pressure. The residue was then purified by flash chromatography (AcOEt/MeOH-99:1) to yield 160 mg of the title compound, 8-phenylmethoxy-3,4-dihydro-5-[2-hydroxy-3-(4-(isobutoxycarbonylamino)-1-piperidyl)-propoxy]carbostyril.

(B) 8-Hydroxy-3,4-dihydro-5-[2-hydroxy-3-(4-(isobutoxycarbonylamino)-1-piperidyl)propoxy]carbostyril 8-Phenylmethoxy-3,4-dihydro-5-[2-hydroxy-3-(4-(isobutoxycarbonylamino)-1-piperidyl)propoxy]carbostyril, the compound from Step A above (160 mg), was dissolved in ethanol (15 mL). Palladium (10% on carbon) was added, and the mixture was stirred under hydrogen at room temperature for 48 hours. The catalyst was removed by filtration, and the solvent evaporated to give 100 mg of crude product which was recrystallized from aqueous ethanol, yielding the title compound, 8-hydroxy-3,4-dihydro-5-[2-hydroxy-3-(4-(isobutoxycarbonylamino)-1-piperidyl)propoxy]carbostyril, m.p. 199°-200° C.

(C) Similarly, proceeding as in part A above, but optionally replacing 5-(2,3-epoxypropoxy)-8-phenylmethoxy-3,4-dihydrocarbostyril with an appropriate compound of Formula 6 wherein $R^2$ is phenylmethoxy, and optionally replacing isobutyl 4-piperidylcarbamate with an appropriate compound of Formula 4, the following compounds of Formula I are prepared:
8-phenylmethoxy-3,4-dihydro-5-[2-hydroxy-3-(4-((cyclopropylmethoxy)carbonylamino)-1-piperidyl)-propoxy]carbostyril;

1-methyl-8-phenylmethoxy-3,4-dihydro-5-[2-hydroxy-3-(4-(ethoxycarbonylamino)-1-piperidyl)propoxy]-carbostyril; and 8-phenylmethoxy-3,4-dihydro-5-[2-hydroxy-3-(4-(isobutoxycarbonyl-N-methylamino)-1-piperidyl)-propoxy]carbostyril.

(D) Similarly, proceeding as in part B above, but optionally replacing 8-phenylmethoxy-3,4-dihydro-5-[2-hydroxy-3-(4-(isobutoxycarbonylamino)-1-piperidyl)propoxy]carbostyril with a compound of Formula I from part C above, wherein $R^2$ is OH, the following compounds of Formula I are prepared:

8-hydroxy-3,4-dihydro-5-[2-hydroxy-3-(4-((cyclopropylmethoxy)carbonylamino)-1-piperidyl)propoxy]carbostyril;

8-hydroxy-3,4-dihydro-5-[2-hydroxy-3-(4-(ethoxycarbonylamino)-1-piperidyl)propoxy]carbostyril; and 8-hydroxy-3,4-dihydro-5-[2-hydroxy-3-(4-(isobutoxycarbonyl-N-methylamino)-1-piperidyl)propoxy]carbostyril.

(E) 8-Phenylmethoxy-3,4-dihydro-5-[2-(4-((cyclopropylmethoxy)carbonylamino)-1-piperidyl)ethoxy]-carbostyril 5-(2-chloroethoxy)-8-phenylmethoxy-3,4-dihydrocarbostyril (0.7 g), from Preparation 6, and cyclopropylmethyl 4-piperidylcarbamate (0.5 g) were dissolved in dimethylformamide (35 mL) containing potassium carbonate (0.3 g) and lithium bromide (0.3 g). The reaction medium was heated for 34 hours at 110° C., and the solvent was then removed by evaporation under reduced pressure. The residue was dissolved in chloroform (70 mL), and the solution was washed with water (2×40 mL), dried over sodium sulfate, and the solvent was evaporated under reduced pressure. Flash chromatography of the residue, using dichloromethane/methanol (90:10) as eluent, afforded 1 g of the title compound 8-phenylmethoxy-3,4-dihydro-5-[2-(4-((cyclopropylmethoxy)carbonylamino)-1-piperidyl)ethoxy]-carbostyril as a yellow oil (ca. 95%).

(F) 8-Hydroxy-3,4-dihydro-5-[2-(4-((cyclopropylmethoxy)carbamylamino)-1-piperidyl)ethoxy]carbostyril The phenylmethoxy compound (1 g), from Step E above, was dissolved in ethanol (350 mL). Palladium hydroxide was added, and the mixture was stirred under hydrogen at room temperature for 3 hours. The catalyst was removed by filtration, and the solvent was evaporated to give 0.7 g (87%) of crude product which was purified via its hydrochloric acid addition salt, to give 8-hydroxy-3,4-dihydro-5-[2-(4-((cyclopropylmethoxy))-carbamylamino)-1-piperidyl)ethoxy]carbostyril, m.p. 168°–170° C.

(G) Similarly, proceeding as in part E above, but optionally replacing 8-phenylmethoxy-5-(2-chloroethoxy)-3,4-dihydrocarbostyril with an appropriate compound of Formula (7) wherein $R^2$ is phenylmethoxy, and optionally replacing cyclopropylmethyl (4-piperidyl)carbamate with an appropriate compound of Formula (4), the following compounds of Formula I are prepared:

8-phenylmethoxy-3,4-dihydro-5-[3-(4-(isobutoxycarbonylamino)-1-piperidyl)propoxy]-carbostyril;

8-phenylmethoxy-1-methyl-3,4-dihydro-5-[2-(4-(cyclopropylmethoxy)carbonylamino)-1-piperidyl)ethoxy]-carbostyril; and 8-phenylmethoxy-3,4-dihydro-5-[3-(4-(isopropoxycarbonyl-N-methylcarbonylamino)-1-piperidyl)propoxy]carbostyril.

(H) Similarly, proceeding as in part F above, but replacing 8-phenylmethoxy-3,4-dihydro-5-[2-(4-((cyclopropylmethyl)carbonylamino)-1-piperidyl)ethoxy]-carbostyril with 8-phenylmethoxy-3,4-dihydro-5-[3-(4-isobutoxycarbonylamino)-1-piperidyl)propoxy]carbostyril, the following compound of Formula I was prepared:

8-hydroxy-3,4-dihydro-5-(3-(4-(isobutoxycarbonylamino)-1-piperidyl)propoxy]carbostyril.

EXAMPLE 4

Compounds of Formula I wherein $R^4$ is acyloxy (A) 3,4-Dihydro-5-[2-acetyloxy-3-(4-(isobutoxycarbonylamino)-1-piperidyl)propoxy]carbostyril 3,4-Dihydro-5-[2-hydroxy-3-(4-(isobutoxycarbonylamino)-1-piperidyl)propoxy]carbostyril (3 g) was dissolved in pyridine (30 mL) and acetic anhydride (0.9 mL) was added dropwise with stirring. After the addition, the mixture was stirred at room temperature for 12 hours, and the pyridine was then evaporated under reduced pressure. The residue was dissolved in chloroform (100 mL) and the organic solution was washed twice with water (50 mL each) and dried over sodium sulfate. The solvent was then evaporated and the residue recrystallized from isopropyl ether to yield 1.5 g of the title compound, 3,4-dihydro-5-[2-acetyloxy-3-(4-(isobutoxycarbonylamino)-1-piperidyl)propoxy]carbostyril, m.p. 120° C.

(B) 3,4-Dihydro-5-[2-pivaloyloxy-3-(4-(isobutoxycarbonylamino)-1-piperidyl)propoxy]carbostyril A cold solution (0°–5° C.) of 3,4-dihydro-5-[2-hydroxy-3-(4-(isobutoxycarbonylamino)-1-piperidyl)-propoxy]carbostyril (3 g) in pyridine (50 mL) was slowly added to pivaloyl chloride (2 mL). The reaction medium was allowed to return to room temperature and then stirred for 20 hours. The resulting dark brown solution was treated as described in part A above, yielding 3.8 g of the title compound, 3,4-dihydro-5-[2-pivaloyloxy-3-(4-(isobutoxycarbonylamino)-1-piperidyl)propoxy]carbostyril, m.p. 110° C.

(C) Similarly, proceeding as in part A above, but optionally replacing 3,4-dihydro-5-[2-hydroxy-3-(4-isobutoxycarbonylamino)-1-piperidyl)propoxy]carbostyril with an appropriate compound of Formula I wherein $R^4$ is OH, and optionally replacing acetic anhydride with the appropriate acid anhydride of formula (R—CO)$_2$O wherein R corresponds to the desired acyl group, the following compounds of Formula I are prepared:

3,4-dihydro-5-[2-butyryloxy-3-(4-(isobutoxycarbonylamino)-1-piperidyl)propoxy]carbostyril;

3,4-dihydro-5-[2-propionyloxy-3-(4-((cyclopropylmethoxy)carbonylamino)-1-piperidyl)propoxy]carbostyril; and 3,4-dihydro-5-[2-acetyloxy-3-(4-(propoxycarbonylamino)-1-piperidyl)propoxy]carbostyril.

(D) Similarly, proceeding as in part B above, but optionally replacing 3,4-dihydro-5-[2-hydroxy-3-(4-(isobutoxycarbonylamino)-1-piperidyl)propoxy]carbostyril with an appropriate compound of Formula I wherein $R^4$ is OH, and optionally replacing pivaloyl chloride with an appropriate acyl chloride of formula R—COCl wherein R corresponds to the desired acyl group, the following compounds of Formula I are prepared:

3,4-dihydro-5-[2-pivaloyloxy-3-(4-((cyclopropylmethoxy)carbonylamino)-1-piperidyl)propoxy]carbostyril;

3,4-dihydro-5-[2-adamantoyloxy-3-(4-(isobutoxycarbonylamino)-1-piperidyl)propoxy]carbostyril;

3,4-dihydro-5-[2-hexanoyloxy-3-(4-(ethoxycarbonylamino)-1-piperidyl)propoxy]carbostyril.

EXAMPLE 5

Compounds of Formula I as Pure Enantiomers Prepared from Racemic Mixtures of Same (A) L-pyroglutamic acid (38 g, 0.29 mol) in hot (70°–75° C.) isopropanol (300 mL) was added to a solution of a racemic mixture of 3,4-dihydro-5-[2-hydroxy-3-(4-(isobutoxycarbonylamino)-1-piperidyl)propoxy]-carbostyril (123 g, 0.29 mol) in hot isopropanol (1400 mL). The resulting mixture was stirred and heated at 70°–75° C. for 30 minutes, and then allowed to return to room temperature. After 24 hours 63 g of crude L-pyroglutamate salt m.p. 166°–169° C. was recovered and recrystallized twice from isopropanol to give 40 g of the L-pyroglutamate salt, m.p. 173.5°–174.5° C.

(B) The L-pyroglutamate salt (40 g) from part A above was dissolved in water (200 mL); 1N sodium hydroxide was added. The crude (R)(+) free base precipitated and was recovered by filtration (34 g) and then directly converted into (R)(+)-3,4-dihydro-5-[2-hydroxy-3-(4-(isobutoxycarbonylamino)-1-piperidyl)-propoxy]carbostyril hydrochloride, m.p. 232°–234° C., $[\alpha]_D$: +10.7°.

(C) The mother liquors remaining after crystallization of the (R)(+) enantiomer from part A above were concentrated under reduced pressure, the residue was treated with 0.5N sodium hydroxide (500 mL) and the aqueous phase was extracted twice with dichloromethane (250 mL each). Organic extracts were combined, dried over sodium sulfate, and the solvent was then evaporated under reduced pressure. The residue (66.6 g) was dissolved in hot (70° C.) propanol (750 mL). D-pyroglutamic acid (21.5 g) in hot propanol (200 mL) was added. The resulting mixture was heated at 70° C. for 30 minutes then allowed to crystallize for 24 hours. 60 g of crude D-pyroglutamate salt was isolated by filtration and crystallized from isopropanol to give 43 g of D-pyroglutamate salt, m.p. 173°–175° C.

(D) Using the method described in part B above, but starting from the D-pyroglutamate (43 g), isolated in part C above, the (S)(−) compound was prepared and converted into the hydrochloride salt, yielding 28 g of (S)(−)-3,4-dihydro-5-[2-hydroxy-3-(4-(isobutoxycarbonylamino)-1-piperidyl)propoxy]carbostyril hydrochloride, m.p. 231°–233° C.; $[\alpha]_D$: −10.8° C.

(E) Similarly, but replacing 3,4-dihydro-5-[2-hydroxy-3-(4-(isobutoxycarbonylamino)-1-piperidyl)-propoxy]carbostyril with a compound of Formula I wherein R[4] is OH or lower alkyl, and following the procedures described in parts A and B above, the following pure enantiomers of compounds of Formula I were prepared:

(R)(+)-3,4-dihydro-5-[2-hydroxy-3-(4-((cyclopropylmethoxy)carbonylamino)-1-piperidyl)propoxy]carbostyril hydrochloride, m.p. 250°–252° C.; $[\alpha]_D$: +11.07°;

(S)(−)-3,4-dihydro-5-[2-hydroxy-3-(4-((cyclopropylmethoxy)carbonylamino)-1-piperidyl)propoxy]carbostyril hydrochloride, m.p. 255°–257° C.; $[\alpha]_D$: −10.93°; and (S)(−)-3,4-dihydro-5-[2-hydroxy-3-(4-((2-hydroxy-2-methylpropoxy)carbonylamino)-1-piperidyl)propoxy]carbostyril hydrochloride, m.p. 220° C.).

EXAMPLE 6

Preparation of Products of Formula I as Pure Enantiomers from Optically Active Intermediates of Formula 1

(A) (2S)-(+)-(2,3-epoxy)-propoxy-3,4-dihydrocarbostyril

NaH (5 g, 0.124 mol) (50–60% in oil) was added to DMF (100 mL). The mixture was stirred, cooled to 0° and 5-hydroxy-dihydrocarbostyril (20 g, 0.123 mol) in DMF (150 mL) was added dropwise. After the addition, the mixture was stirred at room temperature for 1 hour, and then (2S)-(+) glycidyl tosylate (26.5 g, 0.116 mol) in DMF (120 mL) was added. The mixture was heated at 60° C. for 3 hours, then allowed to cool to room temperature. The solution was poured onto a mixture of ice water and extracted twice with $CHCl_3$ (500 mL each). The organic layer was washed with water and dried over sodium sulfate. Evaporation of the solvent under reduced pressure gave a residue which was chromatographed on silica gel using $CH_2Cl_2/CH_3OH$ 9/1 as eluent to afford 10.1 g (40%) of the title compound, (2S)-(+)-(2,3-epoxy)propoxy-3,4-dihydrocarbostril, m.p. 182°); $[\alpha]_D$: +27.85 (c=1, $CH_3OH$).

(B) Similarly, proceeding as in part A above, but using (2R)-(−) glycidyl tosylate the following compound was prepared:

(2R)-(−)-5-(2,3-epoxy)propoxy-3,4-dihydrocarbostyril, m.p. 182° C.; $[\alpha]_D$: −26.06° (c=1, $CH_3OH$).

(C) (2S)-(+)-5-(2,3-epoxy)-propoxy-3,4-dihydrocarbostyril (2.5 g, 0.0124 mol) of part A above, and isobutyl 4-piperidylcarbamate (2.8 g, 0.0114 mol) of Preparation 4 in isopropanol (75 mL) were heated under reflux for 24 hours. The reaction medium was allowed to return to room temperature. The white solid which precipitated was filtered, dissolved in ethanol and a solution of hydrochloric acid in ethanol was added. The resulting precipitate was collected, washed with ether and dried to give 3.2 g (60%) of (S)(−)3,4-dihydro-5-[2-hydroxy-3-(4-(isobutoxycarbonylamino)-1-piperidyl)propoxy]-carbostyril hydrochloride, m.p. 232° C., $[\alpha]_D$: −10, (c=1, $CH_3OH$).

(D) Similarly, proceeding as in part C above, but replacing (2S)-(+)-5-(2,3-epoxy)propoxy-3,4-dihydrocarbostyril with (2R)-(−)-5-(2,3-epoxy)-propoxy-3,4-dihydrocarbostyril, the following compound was prepared:

(R)-(+)-3,4-dihydro-5-[2-hydroxy-3-(4-(isobutoxycarbonylamino)-1-piperidyl)propoxy]carbostyril hydrochloride m.p. 228° C., $[\alpha]_D$: +10.55 (c=1, $CH_3OH$).

(E) Similarly, proceeding as in part C above but replacing isobutyl 4-piperidylcarbamate with cyclopropylmethyl 4-piperidylcarbamate the following compound was prepared:

(S)-(−)-3,4-dihydro-5-[2-hydroxy-3-(4-((cyclopropylmethoxy)carbonylamino)-1-piperidyl)propoxy]carbostyril hydrochloride, m.p. 255° C., $[\alpha]_D$: −10.93 (c=1, $CH_3OH$).

(F) Similarly, proceeding as in part D above, but replacing isobutyl 4-piperidylcarbamate with cyclopropylmethyl 4-piperidylcarbamate the following compound was prepared:

(R)-(+)-3,4-dihydro-5-[2-hydroxy-3-(4-((cyclopropylmethoxy)carbonylamino)-1-piperidyl)propoxy]carbostyril hydrochloride, m.p. 250° C., $[\alpha]_D$: +11.07 (c=1, $CH_3OH$).

EXAMPLE 7

Conversion of Free Base to Salt (A) 3,4-Dihydro 5-[2-hydroxy-3-(4-(tert-butoxycarbonylamino)-1-piperidyl)propoxy]carbostyril (1 g, m.p. 138° C.) was dissolved in ethanol (10 mL) and acidified with hydrochloric acid-saturated ethanol. The resulting mixture was diluted with 2 volumes of diisopropylether and kept at room temperature for 24 hours. A white precipitate was collected by filtration and washed with ether to give 1,1 g of 3,4-dihydro-5-[2-hydroxy-3-(4-(tert-butoxycarbonylamino)-1-piperidyl)propoxy]carbostyril hydrochloride, m.p. 195°-197° C. (dec.).

(B) Similarly, proceeding as in part A above, but replacing 3,4-dihydro-5-[2-hydroxy-3-(4-(tert-butoxycarbonylamino)-1-piperidyl)propoxy]carbostyril with an appropriate free base of a compound of Formula I, the corresponding hydrochloride salts are prepared.

(C) 3,4-Dihydro-5-[2-hydroxy-3-(4-((cyclopropylmethoxy)carbonylamino)-1-piperidyl)propoxy]carbostyril (1.5 g, m.p. 185° C.) was dissolved in hot ethanol and added to a solution of fumaric acid (1 g) in ethanol (10 mL). The reaction medium was kept at reflux for 5 minutes then left at room temperature overnight. 1.6 g of the desired fumaric acid addition salt was recovered by filtration then further purified by crystallization from a mixture of isopropylether:ethanol (m.p.: 188°-190° C.).

(D) Similarly, proceeding as in part C above, but optionally replacing 3,4-dihydro-5-[2-hydroxy-3-(4-((cyclopropylmethoxy)carbonylamino)-1-piperidyl)propoxy]carbostyril with a compound of Formula I and optionally replacing fumaric acid by another pharmaceutically acceptable organic acid (e.g., acetic acid, propionic acid, glycolic acid, malonic acid, maleic acid, oxalic acid, citric acid, ascorbic acid, lactic acid, benzoic acid, glutamic acid, tartaric acid, cinnamic acid, mandelic acid, methanesulfonic acid, paratoluenesulfonic acid, pamoic acid, salicylic acid, and the like) the corresponding pharmaceutically acceptable organic acid addition salts are obtained.

EXAMPLE 8

In vitro Determination of Effects on the Effective Refractory Period

Right ventricular papillary muscles from guinea-pigs were stimulated at 1 Hz and continuously superfused with physiological salt solution. Ventricular Effective Refractory Period (VERP) was determined after 20 minutes incubation with each concentration of drug, compared with control values and expressed as % increase in VERP. Concentrations of the drug which increased VERP by 15% were calculated from concentration-effect curves and mean values with standard error (s.e.) range computed.

The compounds of Formula I demonstrated activity in this assay. For example, 3,4-dihydro-5-[2-hydroxy-3-(4-((2-methylpropoxy)carbonylamino)-1-piperidyl)propoxy]carbostyril provoked at 15% prolongation of the ventricular effective refractory period (VERP) at concentrations less than $10^{-5}$ mol/liter.

EXAMPLE 9

In vivo Determination of Anti-arrhythmic Effects

The techniques followed to measure in vivo the effects of compounds of Formula I on cardiac electrical activity are an exact replication of those described by POIZOT (ref. cited above). They are adaptations to the guinea-pig of methods previously developed by Lhoste et al. (Eur. Journal of Pharmacology, 39, 171-177, 1976) and by Harper et al. (Cardiovascular Research, 13, 303-310, 1979), in dog and man, respectively, and in vitro by Ellis (Annal. N.Y. Acad. Sci., 64, 552-63, 1956).

In anesthetized, artificially ventilated guinea-pig, surface electrodes are installed for right ventricular stimulation and Electro Cardiogram (ECG) recording (lead II). Afterwards, the heart is paced to determine the ventricular effective refractory period calculated from the maximum driving frequency. After a control period of 15 minutes the antiarrhythmic agent to be studied is injected intravenously at increasing doses and at 30 minute intervals. The ECG parameters, QTc (indicative of action potential duration) and RR (indicative of cardiac frequency) intervals are measured at the end of each 30 minute period and the maximum driving frequency is determined.

Compounds of Formula I induced a prolongation of the QTc and RR intervals of the ECG as well as a decrease in the maximum driving frequency and are therefore effective anti-arrhythmic agents.

EXAMPLE 10

The following example illustrates the preparation of representative pharmaceutical formulations containing an active compound of formula I, e.g., 3,4-dihydro-5-(2-hydroxy-3-(4-(isobutoxycarbonylamino)-1-piperidyl)-propoxy]carbostyril hydrochloride.

CAPSULE FORMULATION

The composition contains:

|  | % wt./wt. |
|---|---|
| Active Ingredient | 20.0% |
| Pregelatinised Starch | 79.5% |
| Magnesium Stearate | 0.5% |

A weight of formulation sufficient to give a suitable dose of active ingredients are mixed and dispensed into capsules.

TABLET FORMULATION

The composition contains:

|  | % wt./wt. |
|---|---|
| Active Ingredient | 20.0% |
| Magnesium Stearate | 0.5% |
| Crosscarmellose Sodium | 4.0% |
| Lactose | 74.5% |
| PVP (polyvinylpyrrolidone) | 1.0% |

The above ingredients with the exception of the magnesium stearate and half of the crosscarmellose sodium are combined and granulated using water as a granulating liquid. The formulation is then dried, mixed with the magnesium stearate and the remaining crosscarmellose sodium and formed into tablets with an appropriate tableting machine.

ORAL SOLUTION FORMULATION

The composition contains:

| Active Ingredient | 250-1500 mg |
|---|---|
| Citric Acid Monohydrate | 105 mg |
| Sodium Hydroxide | 18 mg |
| Flavouring | q.s. |
| Water | to 100 ml |

The citric acid monohydrate and sodium hydroxide are dissolved in a sufficient quantity of water. The active ingredient is dissolved in this solution. Sufficient flavouring is added. A sufficient quantity of water is then added with stirring to provide 100 ml of the solution which is filtered and bottled.

SUPPOSITORY FORMULATION

The composition contains:

| | % wt./wt. |
|---|---|
| Active Ingredient | 1.0% |
| Polyethylene Glycol 1000 | 74.5% |
| Polyethylene Glycol 4000 | 24.5% |

The ingredients are melted together and mixed on a steam bath and poured into molds containing 2.5 g total weight.

PARENTERAL FORMULATION (IV)

| Active Ingredient | 2.5-15.0 mg |
|---|---|
| Dextrose Monohydrate | q.s. to make isotonic |
| Citric Acid Monohydrate | 1.05 mg |
| Sodium Hydroxide | 0.18 mg |
| Water for Injection | to 1.0 ml |

The citric acid monohydrate and sodium hydroxide are dissolved in a sufficient quantity of the water for injection. The active ingredient is dissolved in the resulting solution followed by the dextrose monohydrate. The remainder of the water for injection is added with stirring. The solution is filtered, filled into 1.0 ml ampoules which are sealed. The content of the ampoules is then sterilized by autoclaving.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. A compound of the formula:

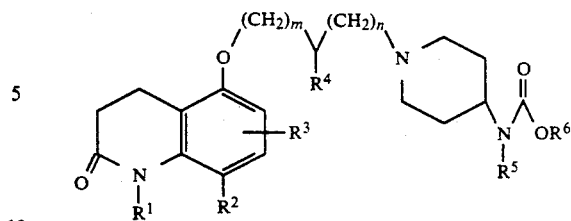

wherein:
m is 0, 1, or 2;
n is 0, 1, or 2;
$R^1$ is hydrogen or lower alkyl;
$R^2$ is hydrogen, halogen, hydroxy, lower alkyl, lower alkoxy, aralkoxy, or acyloxy;
$R^3$ is hydrogen, halogen, lower alkyl, or lower alkoxy;
$R^4$ is hydrogen, hydroxy, lower alkyl, or acyloxy, provided that when $R^4$ is hydroxy or acyloxy, m and n are both 1;
$R^5$ is hydrogen or lower alkyl; and
$R^6$ is alkyl, hydroxyalkyl, alkoxyalkyl, or (dialkylamino)alkyl;
or a pharmaceutically acceptable acid addition salt or N-oxide thereof.

2. A compound of claim 1 as a free base or as an acid addition salt thereof.
3. A compound of claim 2 wherein m is one.
4. A compound of claim 3 wherein $R^4$ is hydroxy and n is one.
5. A compound of claim 4 wherein $R^3$ and $R^5$ are hydrogen.
6. A compound of claim 5 where $R^1$ is hydrogen.
7. A compound of claim 6 wherein $R^2$ is hydrogen.
8. A compound of claim 7 wherein $R^6$ is lower alkyl.
9. A compound of claim 8 wherein $R^6$ is methyl.
10. A compound of claim 8 wherein $R^6$ is ethyl.
11. A compound of claim 8 wherein $R^6$ is propyl.
12. A compound of claim 8 wherein $R^6$ is isopropyl.
13. A compound of claim 8 wherein $R^6$ is butyl.
14. A compound of claim 8 wherein $R^6$ is isobutyl.
15. The (S) enantiomer of the compound of claim 14.
16. The (R) enantiomer of the compound of claim 14.
17. A compound of claim 8 wherein $R^6$ is tert-butyl.
18. A compound of claim 8 wherein $R^6$ is cyclopropylmethyl.
19. A compound according to claim 18 having the configuration (S).
20. A compound according to claim 18 having the configuration (R).
21. A compound of claim 7 wherein $R^6$ is isopentyl.
22. A compound of claim 7 wherein $R^6$ is tert-pentyl.
23. A compound of claim 7 wherein $R^6$ is cyclopentylmethyl.
24. A compound of claim 7 wherein $R^6$ is 4-hydroxybutyl.
25. A compound of claim 7 wherein $R^6$ is 2,2-dimethyl-2-hydroxyethyl.
26. The compound according to claim 25 having the configuration (S).
27. A compound of claim 7 wherein $R^6$ is 2-methoxyethyl.
28. A compound of claim 7 wherein $R^6$ is diethylaminoethyl.
29. A compound of claim 4 wherein $R^1$, $R^2$ and $R^3$ are hydrogen, $R^5$ is methyl, and $R^6$ is isobutyl.

30. A compound of claim 4 wherein $R^1$, $R^2$ and $R^3$ are hydrogen, $R^5$ is isobutyl, and $R^6$ is isobutyl.

31. A compound of claim 6 wherein $R^2$ is hydroxy.

32. A compound of claim 31 wherein $R^6$ is isobutyl.

33. A compound of claim 6 wherein $R^2$ is methoxy.

34. A compound of claim 33 wherein $R^6$ is isobutyl.

35. A compound of claim 33 wherein $R^6$ is cyclopropylmethyl.

36. A compound of claim 6 wherein $R^2$ is methyl.

37. A compound of claim 36 wherein $R^6$ is isobutyl.

38. A compound of claim 36 wherein $R^6$ is cyclopropylmethyl.

39. A compound of claim 5 wherein $R^1$ is methyl, and $R^2$ is hydrogen.

40. A compound of claim 39 wherein $R^6$ is isobutyl.

41. A compound of claim 3 wherein $R^4$ is acyloxy and n is one.

42. A compound of claim 41 wherein $R^2$ and $R^5$ are hydrogen.

43. A compound of claim 42 wherein acyloxy is acetyloxy.

44. A compound of claim 43 wherein $R^6$ is isobutyl.

45. A compound of claim 42 wherein acyloxy is pivaloyl.

46. A compound of claim 45 wherein $R^6$ is isobutyl.

47. A compound of claim 3 wherein $R^4$ is hydrogen.

48. A compound of claim 47 wherein n is zero.

49. A compound of claim 48 wherein $R^5$ is hydrogen.

50. A compound of claim 49 wherein $R^1$ and $R^3$ are both hydrogen.

51. A compound of claim 50 wherein $R^2$ is lower alkyl or lower alkoxy.

52. A compound of claim 51 wherein $R^6$ is lower alkyl.

53. A compound of claim 52 wherein $R^6$ is cyclopropylmethyl.

54. A compound of claim 53 wherein $R^2$ is methoxy.

55. A compound of claim 53 wherein $R^2$ is methyl.

56. A compound of claim 3 wherein n is 0, and $R^6$ is cyclopropylmethyl.

57. A compound of claim 56 wherein $R^1$, $R^2$, $R^3$, $R^4$ and $R^5$ are hydrogen.

58. A compound of claim 56 wherein $R^1$, $R^3$, $R^4$ and $R^5$ are hydrogen, and $R^2$ is chloro.

59. A compound of claim 56 wherein $R^1$, $R^2$, $R^3$ and $R^5$ are hydrogen, and $R^4$ is methyl.

60. A compound of claim 56 wherein $R^1$, $R^3$, $R^4$ and $R^5$ are hydrogen, and $R^2$ is phenylmethoxy.

61. A compound of claim 56 wherein $R^1$, $R^3$, $R^4$ and $R^5$ are hydrogen, and $R^2$ is hydroxy.

62. A compound of claim 56 wherein $R^1$, $R^2$, $R^4$ and $R^5$ are hydrogen, and $R^3$ is methyl.

63. A compound of claim 56 wherein $R^1$, $R^4$ and $R^5$ are hydrogen, $R^2$ is methoxy, and $R^3$ is methyl.

64. A compound of claim 56 wherein $R^1$, $R^4$ and $R^5$ are hydrogen, $R^2$ is methyl, and $R^3$ is methyl.

65. A compound of claim 3 wherein n is 0, and $R^6$ is isobutyl.

66. A compound of claim 65 wherein $R^1$, $R^2$, $R^3$, $R^4$ and $R^5$ are hydrogen.

67. A compound of claim 65 wherein $R^1$, $R^3$, $R^4$ and $R^5$ are hydrogen, and $R^2$ is methoxy.

68. A compound of claim 3 wherein n is 1, and $R^4$ is hydrogen.

69. A compound of claim 68 wherein $R^1$, $R^3$, and $R^5$ are hydrogen.

70. A compound of claim 69 wherein $R^6$ is isobutyl.

71. A compound of claim 70 wherein $R^2$ is hydrogen.

72. A compound of claim 1 as the monohydrochloride salt.

73. A pharmaceutical formulation useful in treating a mammal having a disease-state which is characterized by cardiac arrhythmia, comprising a therapeutically effective amount of a compound of claim 1 and a pharmaceutically acceptable excipient.

74. A method for treating a mammal suffering from cardiac arrhythmia, which comprises administering a therapeutically effective amount of a compound of claim 1.

75. The method of claim 74, which comprises treating a mammal suffering from: supraventricular premature beat, heart block, atrial fibrillation, atrial flutter, atrial tachyarrhythmia of other etiology, atrioventricular nodal or atrioventricular junctional arrhythmias, ventricular premature beats, torsades de pointes, ventricular tachyarrhythmia, ventricular fibrillation, or to prevent sudden death after myocardial infarction or in congestive heart failure.

76. The method of claim 74, which comprises treating a mammal suffering from: supraventricular arrhythmia, ventricular tachycardia, or junctional re-entry arrhythmia.

77. The method of claim 75 wherein:
heart block is selected from the group: first degree heart block, second degree heart block and complete heart block; and
ventricular premature beats is selected from the group: unifocal ventricular premature beats and multifocal ventricular premature beats.

* * * * *